US00RE41394E

(19) United States
(12) Reissued Patent
Bugge et al.

(10) Patent Number: US RE41,394 E
(45) Date of Reissued Patent: Jun. 22, 2010

(54) IMPLANTABLE DEVICE FOR UTILIZATION OF THE HYDRAULIC ENERGY OF THE HEART

(76) Inventors: Mogens Bugge, Dalheimersgatan 2A, 113 20 Goteborg (SE); Goran Palmers, Hallstamsvagen 35, 436 Askim (SE)

(21) Appl. No.: 11/333,750

(22) Filed: Jan. 17, 2006

Related U.S. Patent Documents

Reissue of:
(64) Patent No.: 6,827,682
Issued: Dec. 7, 2004
Appl. No.: 10/026,224
Filed: Dec. 19, 2001

U.S. Applications:
(63) Continuation of application No. PCT/SE00/01355, filed on Jun. 26, 2000.

(30) Foreign Application Priority Data

Jun. 23, 1999 (SE) ..... 9902381

(51) Int. Cl.
*A61M 1/10* (2006.01)

(52) U.S. Cl. ..... 600/16; 623/3.1
(58) Field of Classification Search ..... 600/16, 600/17; 601/84, 150, 152, 153; 604/65, 66, 604/67; 623/3.1, 3.11, 3.12, 3.16, 3.17, 3.18, 623/3.19, 3.22, 3.23, 3.24, 3.25, 3.27, 3.28, 623/3.3
See application file for complete search history.

(56) References Cited

U.S. PATENT DOCUMENTS 3,563,245 A * 2/1971 McLean et al.
3,667,069 A * 6/1972 Blackshear et al. ..... 623/3.1
3,835,864 A 9/1974 Rasor et al.
3,911,897 A * 10/1975 Leachman, Jr. ..... 600/17
3,966,358 A * 6/1976 Heimes et al. ..... 417/12
4,173,796 A * 11/1979 Jarvik ..... 3/1.7
4,690,143 A 9/1987 Schroeppel
4,938,766 A 7/1990 Jarvik
5,269,811 A * 12/1993 Hayes et al. ..... 623/3
5,282,849 A 2/1994 Kolff et al.
5,314,469 A * 5/1994 Gao ..... 623/3
5,782,910 A * 7/1998 Davidson ..... 623/3

OTHER PUBLICATIONS

International Search Report mailed Oct. 11, 2000 for Application No. PCT/SE00/01355.*

* cited by examiner

*Primary Examiner*—Carl H Layno
*Assistant Examiner*—Frances P Oropeza
(74) *Attorney, Agent, or Firm*—Ostrolenk Faber LLP

(57) ABSTRACT

A device, potentially implantable in a living organism, intended to utilize at least a part of the hydraulic energy generated by the heart (10)—the primary unit—at the natural phases of work when the cavities of the heart (11, 12 and 16, 17) are filed with blood. The device includes at least one secondary unit (24), which is connectable to the cardiovascular system of the organism and arranged to utilize said hydraulic energy. The secondary unit is represented by at least one hydraulic motor (24a) arranged to transfer the hydraulic energy to a transferal organ (28). The transferal organ (28) is arranged to influence at least one tertiary unit, for example an executive device (29), which is constructed in order to convert the transferred energy to an alternative form of energy, with the purpose to influence certain defined functions within the organism. Preferably is arranged a regulating device (30) in order to control running parameters of the unit.

24 Claims, 16 Drawing Sheets

IMPLANTABLE DEVICE FOR UTILIZATION OF THE HYDRAULIC ENERGY OF THE HEART

Matter enclosed in heavy brackets [ ] appears in the original patent but forms no part of this reissue specification; matter printed in italics indicates the additions made by reissue.

CROSS REFERENCE TO RELATED APPLICATIONS

This application is a continuation of PCT International Application No. PCT/SE00/01355 filed Jun. 26, 2000 which PCT Application claims priority to Swedish Application No. 990238 1-4 filed June 23, 1999.

The present invention refers to a device, implantable in a living organisms, for the utilisation of at least part of the hydraulic energy developed by the heart (the primary unit), which is acquired by the natural work of the heart i.e. by the contraction of the heart (the systolic phase) where the blood is put under pressure, followed by the relaxation phase (the diastole), where the ventricles of the heart are filled with blood. The device comprises at least one secondary unit connected to the cardiovascular system.

THE BACKGROUND AND PROBLEMS OF THE INVENTION

The heart is well known to work as two deplacement pumps which are functionally separated apart, and which work sycncronously, in the way that the right pump transports blood to the pulmonary circulation, whereafter the oxygenated blood returns to the left pump. Thereafter, the left side ejects the oxygenated blood to the peripheral circulation of the body i.e. to the vascular system of the entire organism. Finally, the blood returns to the inlet of the right pump.

The force of the pump is generated by the contraction of the cells of the myocardium, which surrounds the atria and the ventricles of the heart. The direction of the circulation is controlled by unidirectionally acting valves. The energy delivered by the heart to the surrounding, mainly to the blood consists primarily of pressure-volume work against the blood, kinetic work and heat.

It is previously known to assist the circulation, when the heart is fainting, by external force. Such assist is typically powered by pressurized air or electricity as energy source located outside the body. It has even been suggested to utilize energy converted from muscle, other than the heart, for example muscle of the legs, or from the back, as energy for the circulating blood via some sort of converting mechanism.

To add energy, from outside the body, to implanted assist devices has previously been used and is principally not difficult. But it may cause discomfort and be complicated for the patient due to tubings and cables penetrating the skin. Such connections limit the patient's degree of freedom to special rooms or to trolleys equipped with batteries and computers. If therefore, one could use energy existing within the body, the patient would experience a new degree of freedom. The circulation of living creatures, including man, is normally kept in balance between the cardiac output and the resistance of the peripheral arteries, in the way that blood pressure is kept within narrow limits. This is necessary since several organs cannot work and/or survive if the blood pressure drops below, or increases above extreme levels. The kidneys and the brain are organs known to be sensitive to variations in blood pressure. Thus, if the heart in a human being faints, and cannot pump out the blood with enough force to keep the arterial mean blood pressure slightly above 50 mm Hg, the person will loose consciousness. If the kidneys are exposed for a similarly low arterial pressure, at least if exposed for a considerable long time, the urine production will cease. When the heart is fainting, and for some reason or another cannot generate a sufficiently high blood pressure, the person will die. This is through for left side fainting, but also for right side fainting if the right pump cannot overcome the resistance of the lungs.

The fact that the heart sometimes cannot pump out the blood to the circulation with a sufficiently high pressure does not necessarily mean that the heart cannot deliver enough energy to the circulation, if mechanical, and other conditions, where correct. In contrary, several examples can be given, where the heart is extremely powerful and has hypertrophied to a size 2–3 times the normal, over years, but still the pressure is low. One typical example for such a situation, is a heart with one or more valves leaking, or a dilated heart, which cannot deliver a sufficiently high pressure to the circulation. The energy consumption of such a heart is much higher than the normal delivery to the circulation at rest (1 watt). The efficiency, i.e. the PV-energy+the kinetic energy/ the total energy for a normal heart is around 15%, while for a diseased heart, especially if dilated the efficiency is considerably lower than that.

A normal heart has a relatively low efficiency as a pump, compared to industrial pumps. Energy losses do arise (among other things) since the ventricles, at each contraction, as first step, have to generate a contraction of the ventricular wall, which allows the ventricular pressure to reach the aortic pressure (or the pressure of the pulmonary artery for the right pump); the ventricle wall is pre-tightened. This contraction leads to energy losses, which are proportional to the diameter of the ventricles in square, and therefore, these losses are great when the ventricles are dilated. In the second phase of the contraction, the ventricles have to increase the tension of the ventricular wall further, resulting in a ventricular pressure higher than the aortic pressure whereby the ejection of the blood takes place. During the ejection, the volume of the ventricles decreases, and therefore, the wall thickness of the ventricles increases. This remodeling of the muscle mass also leads to energy losses which in some diseases (for example at extremely hypertrophic hearts) may be considerable.

The way more than normal energy can be extracted from a fainting heart, is realized by comparing the pressure volume relation demonstrated in FIG. 1, which is en example given for a healthy heart (with an ejection fraction of 80%), with the relation given in FIG. 2, for a diseased heart (with an ejection fraction of 40%). Both figures are presented as PV-diagrams. The pressure-volume curve appears as a modified square anti-clockwise and the area within the loop represents the work of the heart (EW=External Work) on the blood. The area PE represents energy within the heart converted to heat at each contraction of the heart, which therefore is to be considered as wasted energy.

It is noted that the area of the surface PE (in FIGS. 1, 2 and 3) is not directly correlated to the one of the EW surface. The PE-area is proportional against the wasted energy but must be multiplied by a factor over 10 in a weak heart.

FIG. 2 is an example of how a diseased heart works. In order to achieve same minute volume and frequency as a healthy heart, blood is retained within the ventricle after each contraction and even the mean pressure is below normal level. The efficiency of the heart is decreased.

The fact that retained blood within the ventricle after each contraction does lead to energy loss should not be considered as if the retained blood should possess potential energy released in diastole. This is not the case since the blood is not compressible. In contrast, energy is lost since the ventricle must be pre-tightened before it can create a pressure high enough to start the ejection of the blood. This pre-tightening is well known energy consuming and is proportional to the volume of the ventricle.

Besides this factor, there are several other important factors that decide the oxygen consumption of the heart and thereby the energy consumption, the magnitude of the lost energy and the efficiency of the heart. These are described in the book "The Heart Arteries and Veins" 8 Edition. McGraw-Hill Inc., being for example the mass of the heart, the level of the pre-tightening, the frequency of the heart and the hormones influencing the heart. In contrast, as a paradox, the external work of the heart is not the main factor to decide the oxygen consumption since maximally 15% of the energy of the heart is converted to external work (for a healthy heart). When a heart wakens, often first step is a dilatation of the ventricle, later through an increase of its mass whereby the losses increase dramatically.

The idea to take out more blood at the contraction of the ventricles (systolic phase) is old and used every day. Pharmacologically it is easy to dilate the capacitance vessels of the arterial system (i.e. an afterload reduction) and thereby increase the stroke volume and the minute volume. But the price is low blood pressure and the limits within one operates are narrow. Likewise, one can influence the heart mechanically to eject more blood in each cycle. This may for example be achieved by diastolic counterpulsating, and one example of such pumps is the aortic balloon pump.

A diastolic counterpulsator works in its simplest form in the way that when the heart in systolic phase ejects its contained blood, the counterpulsator accumulates part of this volume outside the cardiovascular system for example in a pump cylinder connected to the artery in a groin. Thereby, the systolic resistance is reduced and the systolic blood pressure is kept low which ameliorates the ejection of the blood from the heart.

In diastolic phase, when the valve between the heart and the arterial system is closed, an external force, i.e. a motor, is used to press back the blood from the counterpulsator to the arterial system. The diastolic pressure is increased, as is the mean pressure. It is noted that this way of pumping results in a mirrored arterial blood pressure curve. This is true for external counterpulsators as described above, but also for internally located counterpulsators like the aortic balloon pump, which is the most commonly used assist pump in modern cardiac surgery. The mechanism is simple and intelligent—bit it needs externally added energy.

The counterpulsator is a device well described in the medical literature i.e. "Cardiopulmonary Bypass" by Kenneth M. Taylor, 1986. Chapman and Hall Ltd., 9 chapter.

By U.S. Pat. No. 4,938,766—R. Jarvik—is known an implantable prosthesis—a device—for amelioration of the perfusion of the natural cardiovascular system without adding energy from outside the body. However, the device cannot store the energy for more than part of a cardiac cycle. Nor can it render the arterial pressure curve in mirrored version, which is the case for the counterpulsator. It flattens out the blood pressure curve. It may increase the mean pressure in the arterial system, and it may enhance the take out of more energy from the heart (more than before connecting the device), but it will decrease the maximum systolic pressure. Thus, the device cannot solve the pressure demand from peripheral organs like the brain and the kidneys, which have an absolute pressure demand in order to survive.

The Purpose Of The Invention And The Solution Of The Problem

The purpose of the present invention is to achieve a device which, as mentioned in the introduction, without adding external—from outside the body—energy, can utilize energy created within the body, for different purposes and in different ways, depending on which disease is actual. Some examples of possibilities to be opened are given:

- to correct a diseased heart, by correcting the pump modus of the heart in the way that the PE is decreased;
- to make possible, in patients with edema, like for example in patients with ascites, a system to eliminate the edema without control mechanisms;
- to control and manipulate natural and artificial openings of the body;
- to supply implanted apparatus like pacemakers, electric pulsgenerators like ICD apparatus with power;
- to supply computers or similar equipment with energy in order to control implanted electronic equipment which may be in contact with the central nervous system etc.

The purpose is among other to bring back the modus operandi of the heart to a normal pump modus and thereby reduce the lost energy, while the energy delivered to the surrounding (at rest) is constant. These purposes have been solved by the characteristics mentioned in the patent claims.

DESCRIPTION OF THE DRAWINGS

The invention will be described in detail below together with some examples with referral to enclosed drawings.

GENERAL DESCRIPTION OF THE INVENTION

Figure 1:
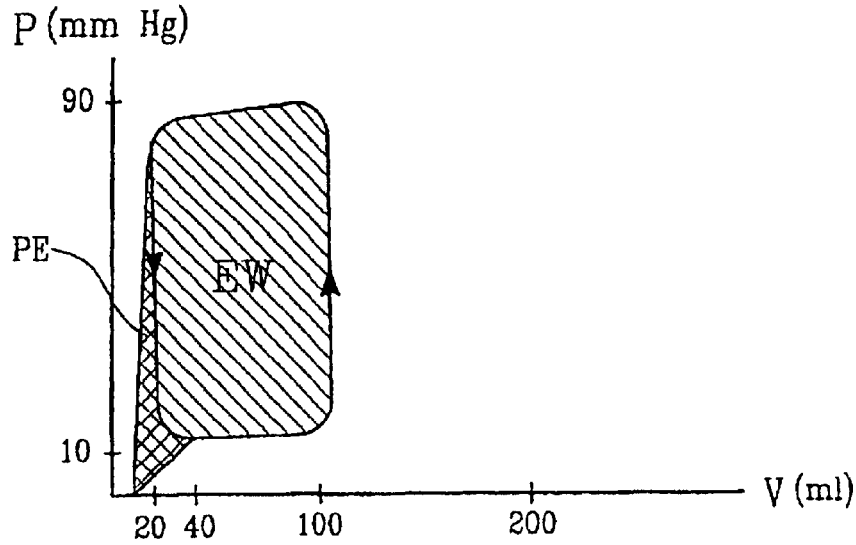
FIG. 1 demonstrates a pressure—volume—diagram (PV—diagram) of a healthy heart.
Figure 2:
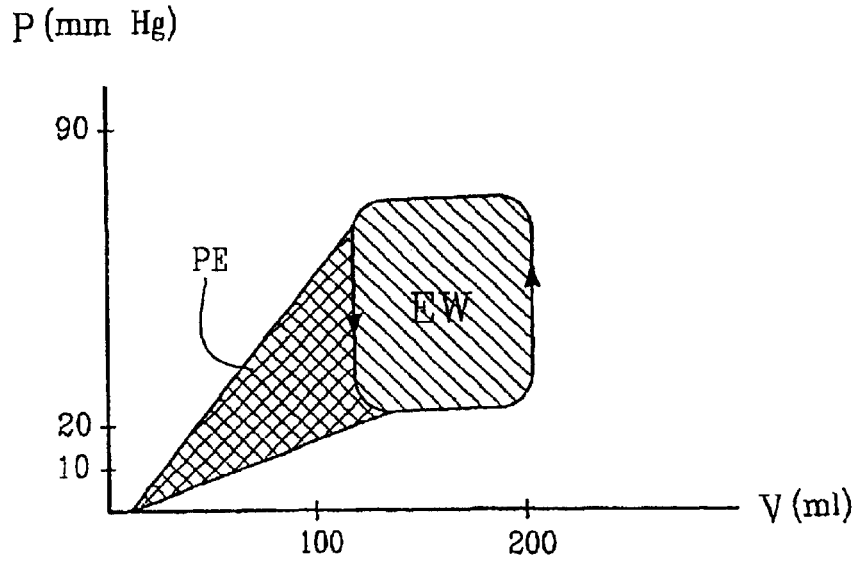
FIG. 2 demonstrates a similar PV—diagram for a fainting heart.
Figure 3:
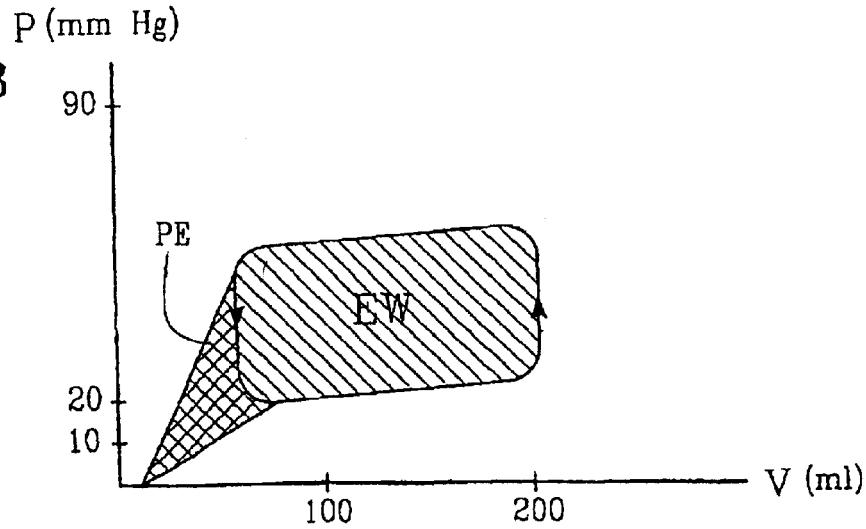
FIG. 3 demonstrates a diagram similar to FIG. 2, for a fainting heart, corrected with the device according to the present invention.

The main purpose of the invention is to utilize and/or to convert at least part of the energy delivered by the heart—also called the primary unit—to the blood for specific or other purposes, primarily within the body, but in some specific cases even outside the body. The device needed to extract energy from the pump work of the heart via the blood depends on the purpose the energy is intended to be used for and consists in most cases a conventional hydraulic motor—even called the secondary unit—which has been adjusted according to its specific purpose. The hydraulic motor, which is powered by the pressurized blood, converts the hydraulic energy back to mechanical or electric energy. After this conversion, the energy can be used immediately, stored for a short period (a cycle of the heart) or stored for a longer time. The energy can be used to run different apparatus i.e. one or more pumps, an electric motor, a control mechanism or a regulator etc. The actual equipment will decrease the pressure within the heart, Ph and the residual volume Vr after the contraction of the ventricle/ventricles.

If the hydraulic energy is converted within the body to electricity, new possibilities will appear for self supply with limited amounts of electric power, to be used for several purposes, for example to run pumps to maintain the circulation, to generate blood pressure higher than the normal pressure, generated by the normal or by the diseased heart etc.

The energy delivered by the heart to a hydraulic motor is V*dp where V is volume and dp is reduction in pressure of the blood when passing the hydraulic motor. The energy spent by the heart to deliver V*dp is much higher than V*dp itself.

One way to absorb energy from the pressurized blood is by help of a hydraulic motor connected to the heart directly, normally to one or both ventricles, and most frequently to the left ventricle. But principally, any of the atria and ventricles of the heart may be connected to each its motor and work independently or more or less interconnected.

By adjusting the characteristics of the hydraulic motor, more blood may be ejected the natural way and to the motor than before connection to the device. The pressure in the heart may be same as normal—or lower, depending on the characteristics of the motor. At diastole, the ventricle needs to be filled with blood, and the most natural way to do this is to empty the motor directly through the inflow connection, which in that case will be the outflow connection as well. Thus, the blood from the motor is mixed with the blood filling the ventricle the natural way. But emptying an filling of the motor does necessarily have to take place by the same route. If the motor empties its blood "upstream" in the circulation, the blood will automatically find its way down to the same ventricle (although it may be a burden for the circulatory system to a certain degree on its way back).

As mentioned, the energy absorbed from the heart by the motor may be used for several purposes. One example is to lead back the energy directly to the circulation—or later, at the same time as electricity is generated and stored in an accumulator. Arranged in this way, the net amount of energy transferred to the circulation will be the same, less or more than before connection to the motor. The profile of the blood pressure can be manipulated and the mean blood pressure can be increased.

It is even possible with this device to take out a maximum of blood volume for the ventricle at a pressure so low that the valve between the ventricle and the circulation never opens, which normally is inconsistent with life, and still absorb energy at this low pressure. The device may give back the energy to the circulation and thereby generate a sufficiently high pressure to guarantee life —without adding energy from the surrounding.

DESCRIPTION OF SOME EXAMPLES

Figure 4:
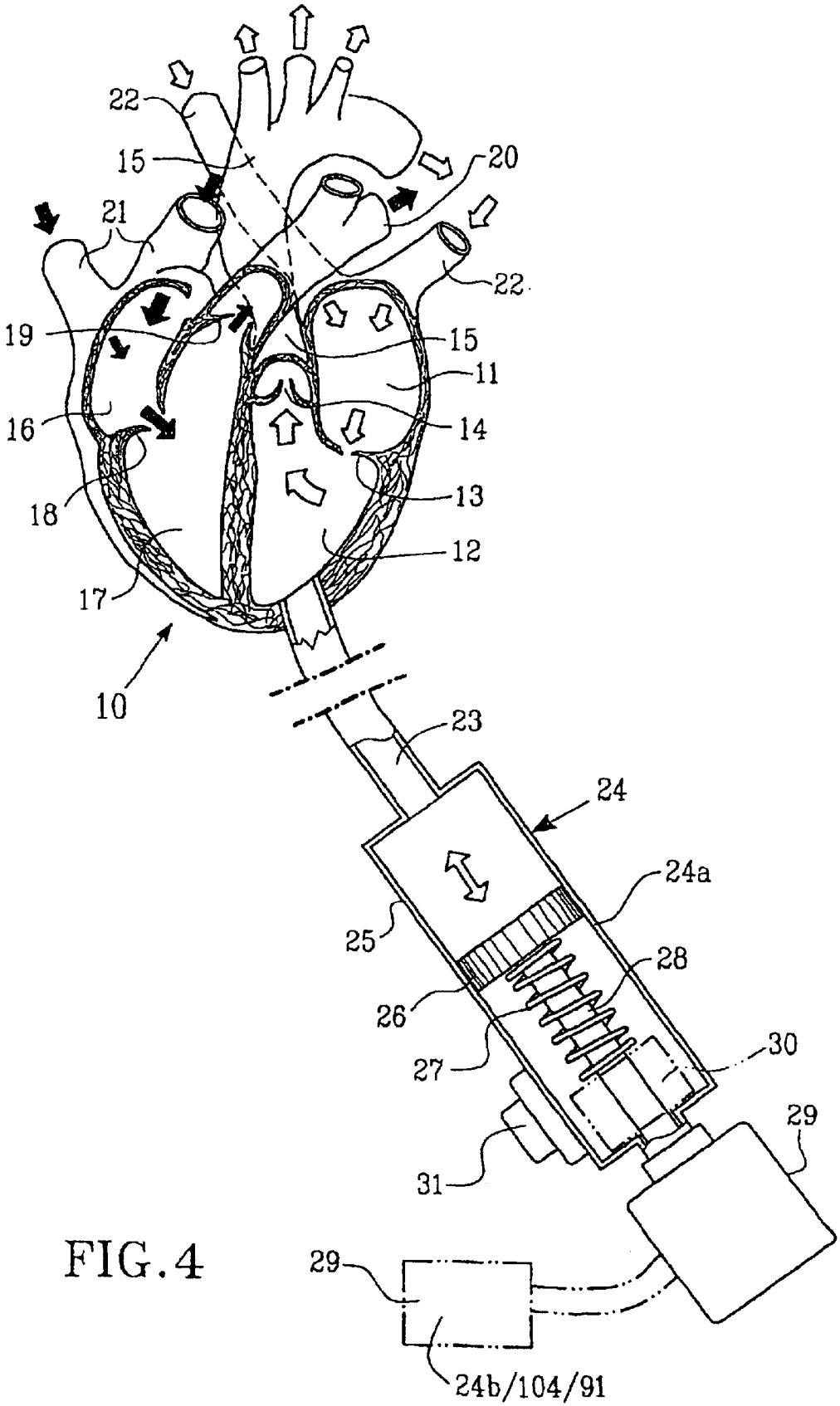
FIG. 4 demonstrates a heart seen from its anterior aspect and partly in a 3 dimensional way and applied with a very schematic device according to a first variant of the present invention.

To get e better understanding of the invention, FIG. 4 demonstrates a human heart 10 partly in a 3 dimensional presentation, where 11 indicates the left atrium, 12 the left ventricle, 13 the mitral valve, 14 the aortic valve, 15 the main body artery (the aorta), 16 the right atrium, 17 the right ventricle, 18 the tricuspid valve, 19 the pulmonary valve, 20 the pulmonary artery, 21 two caval veins and 22 four pulmonary veins.

The blood is pumped from the circulatory system of the body (the periphery) via the two caval veins 21 to the right atrium 16, passes through the tricuspid valve 18 to the right ventricle 17 and is pumped through the pulmonary valve 19 to the pulmonary artery. In the lungs the blood absorbs oxygen and continues its flow to the pulmonary veins 22 to the left atrium 11 and further via the mitral valve 13 to the left ventricle 12, which pumps out the blood through the aortic valve 14 to the main body artery 15.

To the lower part of the left ventricle 12 is connected, i.e. by an operation, a connection tube 23, which connects the heart 10—the primary unit—with an implanted secondary unit 24. This is illustrated in a considerably greater scale than the heart and is in this example a hydraulic motor 24a. Its plus side is a variable volume chamber i.e. a cylinder 25 and within the cylinder is an axially movable piston 26, which on its minus side is influenced by a return spring 27. This spring tends to move the piston to its one end at the opening of the connection tube 23, when the hydraulic pressure of the heart comes to an end. In stead of a cylinder the hydraulic motor may consist of a bellows cylinder or a similar device. To the piston 26 is connected a transferal organ 28, which in FIG. 4 consists of a piston rod the purpose of which is to transfer at least part of the hydraulic energy generated by the heart to one or more executing device 29, also called tertiary units.

In most applications it is an advantage if the return spring 27 is adjustable concerning spring force as well as other spring characteristics, which in FIG. 4 is indicated by 30, which is a regulating mechanism. It is even possible to influence the regulator 30 form outside the body by for example radio transmission.

Figure 5:
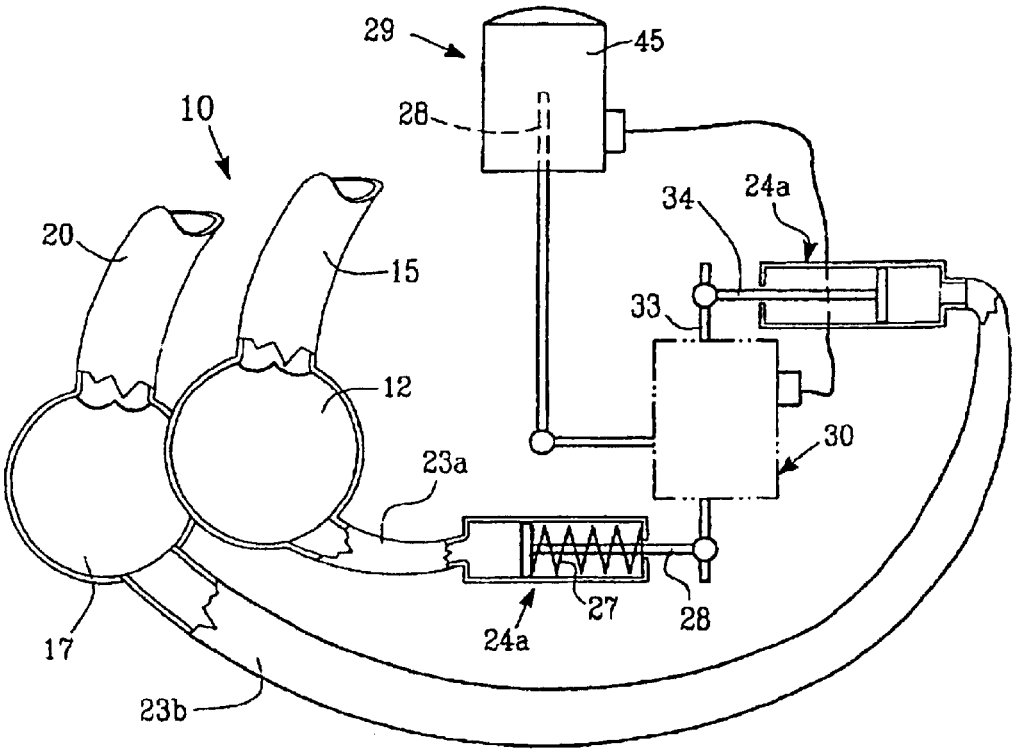
FIG. 5 demonstrates schematically a second variant of a device according to the present invention with two hydraulic cylinders working parallel to each other.

FIG. 5 demonstrates an example, where body ventricles of the heart 12 and 17, very schematically, are illustrated and where the left ventricle 12 via a tube 23a is connected to a secondary unit 24, which may be a hydraulic motor 24a, while the right ventricle 17, via the tube 23b, is connected to another hydraulic motor. The transferal organ 28 is a piston rod connected to a lever 33, which is part of the regulating mechanism 30, containing the gear mechanism 32 to be described later under FIG. 15. The generated energy may be taken out from the tertiary unit 29, which for example may be an electric generator.

In systolic phase, when the heart contracts, blood is pumped from both ventricles of the heart 12 and 17 to each its hydraulic cylinder 24a, and the pistons are pressed back while the return spring 27 is compressed. In diastolic phase (the relaxation phase of the heart where the pressure of the ventricles drops) the pistons are pressed back by the spring 27 and the blood returns to the heart. Depending on the adjustment of the gear, the quote of energy extracted from the two ventricles may be varied.

Figure 6:
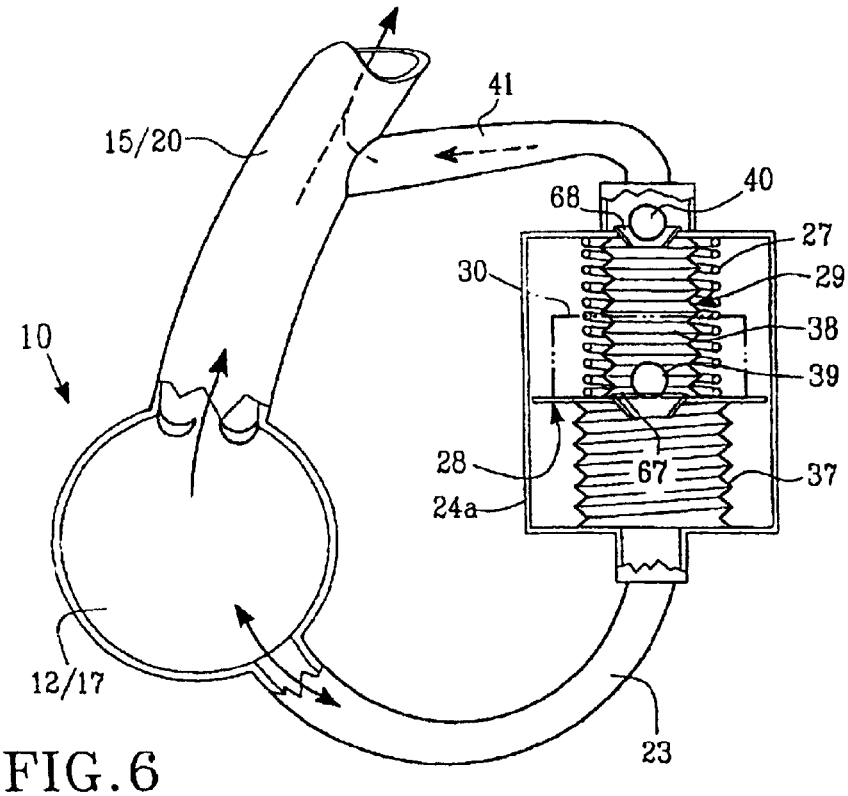
FIG. 6 demonstrates a third variant of the invention by a device for pressure amplification using a double bellow device.

FIG. 6 demonstrates an example where the hydraulic motor 24a is arranged as a unidirectionally acting pressure box, in the form of two bellows 37 and 38 connected in series, and with different cross sectional area resulting in a device working as a differential piston. The bellows expand longitudinally against a return spring 27 being part of the regulating mechanism. Between the first bigger bellows 37, connected directly to the ventricle 12 or 17, and the minor bellows 38 is arranged a pusher plate, being in this example the transferal organ 28. In the pusher plate is an opening 67, where a valve 39 is located, which opens in diastole. At the end plate of the minor bellows 38 is an opening 68 for emptying of the device with another valve 40. This valve is influenced to open by the pressurized blood during systolic phase, at the same time as the return spring 27 is compressed.

In systolic phase, the pressurized blood is transferred from the ventricle 12/17 to first bellows 37 and to the transferal organ 28. First valve 39 is closed and bellows 37 expands. At the same time, blood is transferred from the second bellows 38 via the tube 41 to the artery 15/20 through the open valve 40. It is noted that the pressure in systolic phase is bigger in the second bellows 38 than in the heart 10 and bigger than in the first bellows 37, and that this difference is proportional to the difference in cross sectional area between the two bellows.

In diastolic phase, the valve 40 is closed and the return spring 27 will press the transferal organ 28 in return. The valve 39 opens passively and blood flows from the first bellows 37 to the second bellows 38, at the same time as blood flows back from the first bellows 37 to the heart 12/17 through the tube 23.

Figure 7:
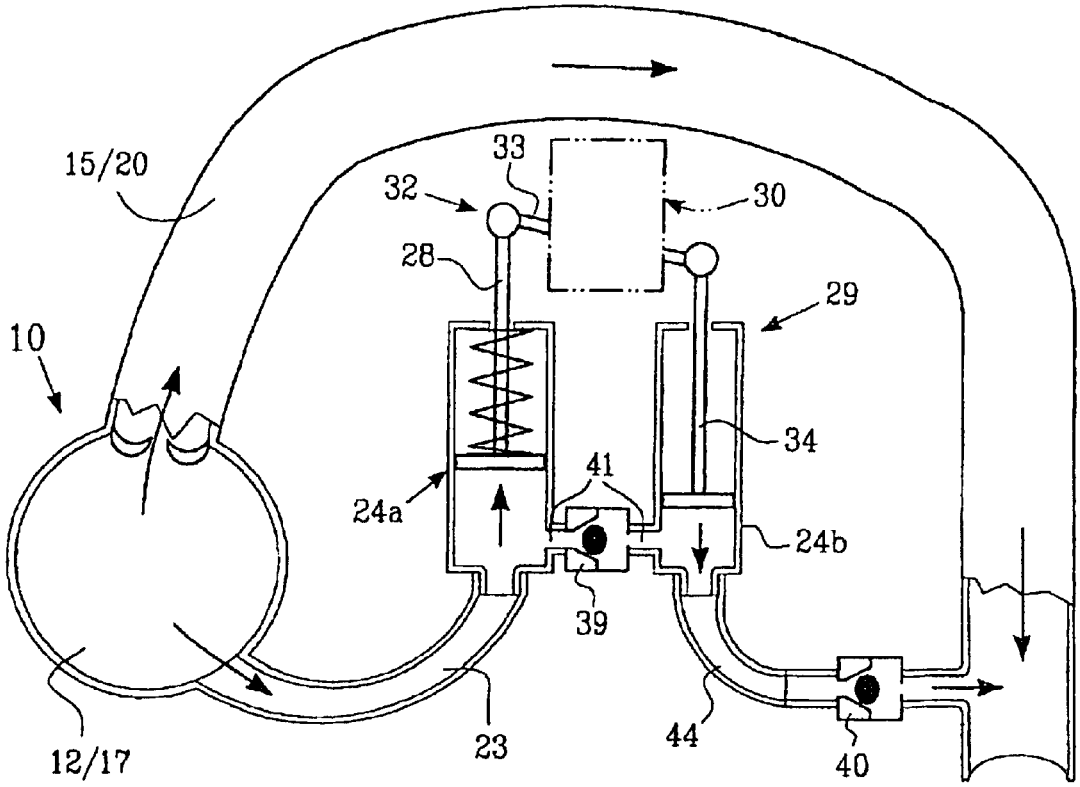
FIG. 7 demonstrates schematically a modified pressure amplifier with blood flow through the hydraulic motor as well as through the hydraulic pump. The device works synchronously with the beats of the heart.

FIG. 7 demonstrates a pressure amplifier with variable degree of amplification, which works synchronously with the heart. The pressure amplifier consists of two hydraulic cylinders connected to each other with variable gear through the regulating mechanism 30. One cylinder 24a works as a motor, and the other 24b as a pump. The hydraulic motor 24a is connected directly to one of the ventricles 12 or 17 and connected to the gear mechanism 30 illustrated in FIG. 15. The pump 24b fills with blood from the same ventricle via the valve 39 and delivers the blood to the aorta via the tube 44 and the valve 40. By arranging the cross sectional area of the cylinders 24a and 24b in the way that the area of the hydraulic motor 24a is bigger than the one of 24b, and by arranging the gear of the regulating mechanism 43 in a proper way, one can get whichever higher pressure in the tube 44 and thereby the intended pressure amplification.

Figure 8:
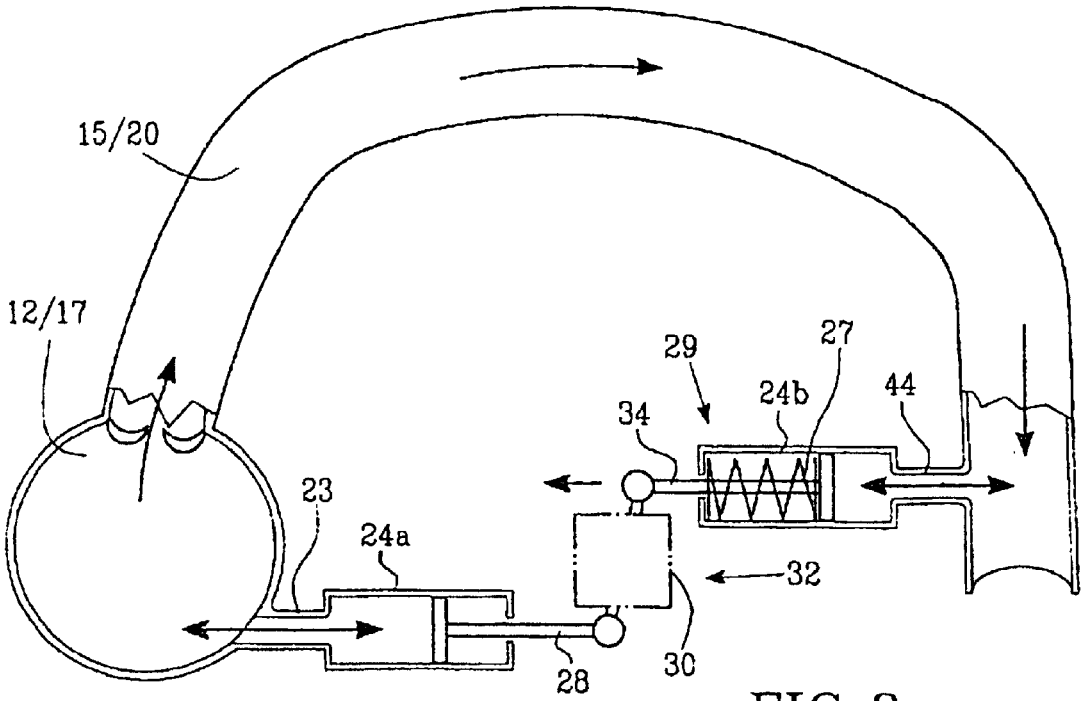
FIG. 8 demonstrates another example of a pressure amplifier where the pump works in counter phase compared to the heart beats, i.e. a counterpulsator.

FIG. 8 demonstrates a counterpulsator intended to accomplish a mirrored blood pressure curve in an artery and accomplish a pressure amplification with variable gear. Two piston pumps 24a and 24b are interconnected via the piston rods 28, 34 and a regulating mechanism 30. One piston pump 24a is directly connected to one of the ventricles 12 or 17 and the piston pump 24b is connected directly to the artery 15 or 20. The regulating mechanism 30 may be adjusted by the regulator 43 (shown in FIG. 15) in the way that the gear i.e. the length of the levers 33 may be adjusted, and thereby the pressure of the tube 44 from the piston pump 24b may be varied. In systolic phase, both piston pumps work as hydraulic motor and deliver their energy to the return spring 27. In diastolic phase, the return spring delivers the majority of its energy to 24b, which then works as a pump. In this example, no valves and no regulating mechanism are needed. The piston pumps 24a and 24b work in counterphase with the beats of the heart in the sense that 24a and 24b work as motors when the heart works as a pump (in systolic phase) but work as pumps when the heart fills with blood (diastolic phase). This is very important for the arterial mean pressure as well as for the arterial pressure in diastole, and thereby for the perfusion of the heart itself (the function of the coronary circulation) which takes place mainly in diastole.

Figure 9:
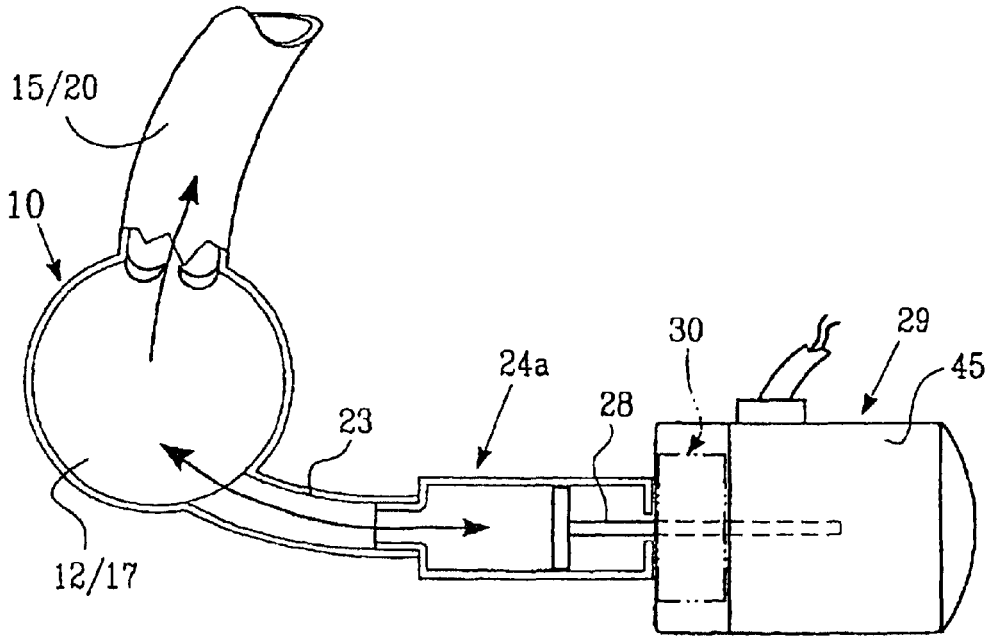
FIG. 9 demonstrates schematically a device according to the present invention for the conversion of force applied by linear motion to electricity.

FIG. 9 illustrates the invention applied for the generation of electricity. The hydraulic motor 24a is provided with a transferal organ 28, which transfers its linear movements to the tertiary unit 29 being a linear generator 45. The generator converts the movements to electricity to be used for influence of other functions within the organism. No valves are needed and the system works independent of arrhythmia like for example atrial fibrillation.

Figure 10:
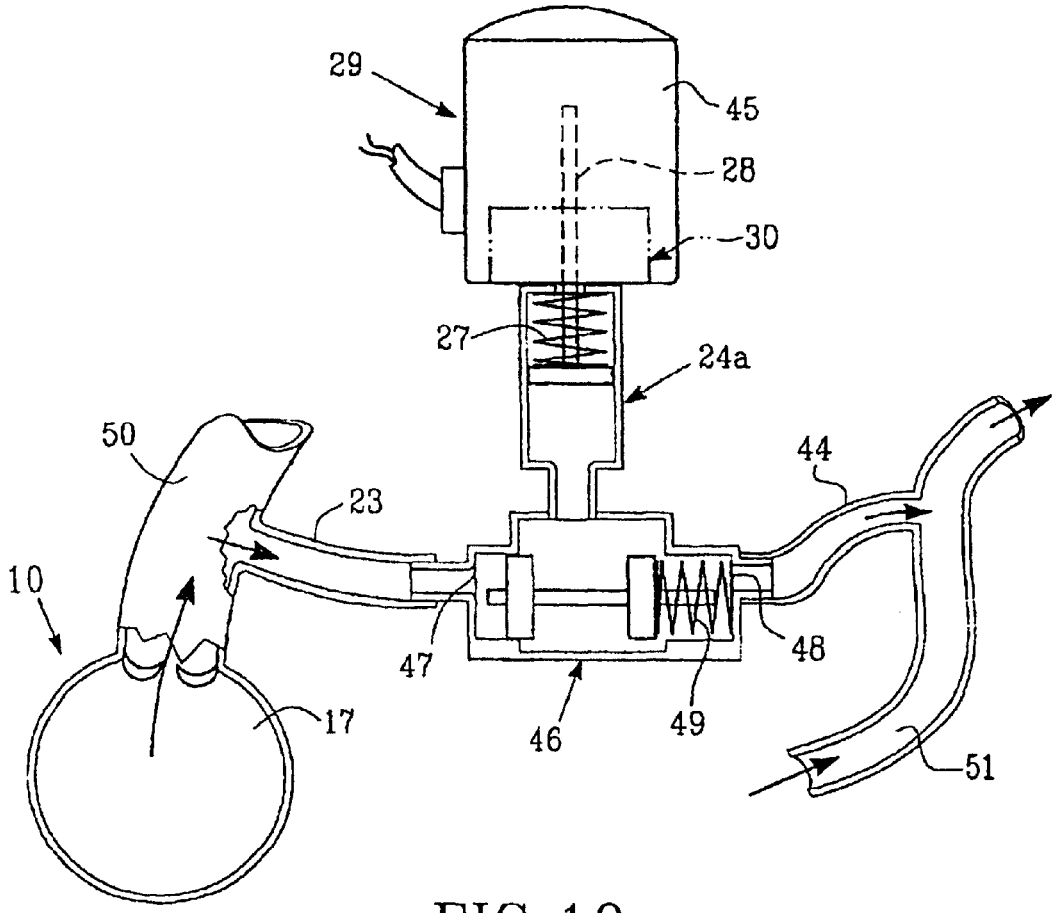
FIG. 10 demonstrates a device for absorption of energy by conduction of blood from the arterial to the venous system.

FIG. 10 demonstrates an example of a device for absorption of energy by transport of blood from the arterial to the venous system. In this case, the device according to the invention is located somewhere in the circulation. A shuttle valve 46 is connected with one port 47 to an artery 50, and with another port 48 to a vein 51. By the function of the shuttle valve it is possible to load the hydraulic cylinder 24a with pressurized blood, which opens the first port 47 while the second port 48 is closed while the spring 49 is compressed. After systolic phase, when the pressure drops below the force of the spring, the second port opens and the accumulated blood can be transferred to the vein 51. The system requires some sort of chock absorption in order to inhibit resonance disturbances. The tertiary unit 29, powered by the transferal organ 28, delivers electricity to be used for influence of other functions within the organism.

Figure 11:
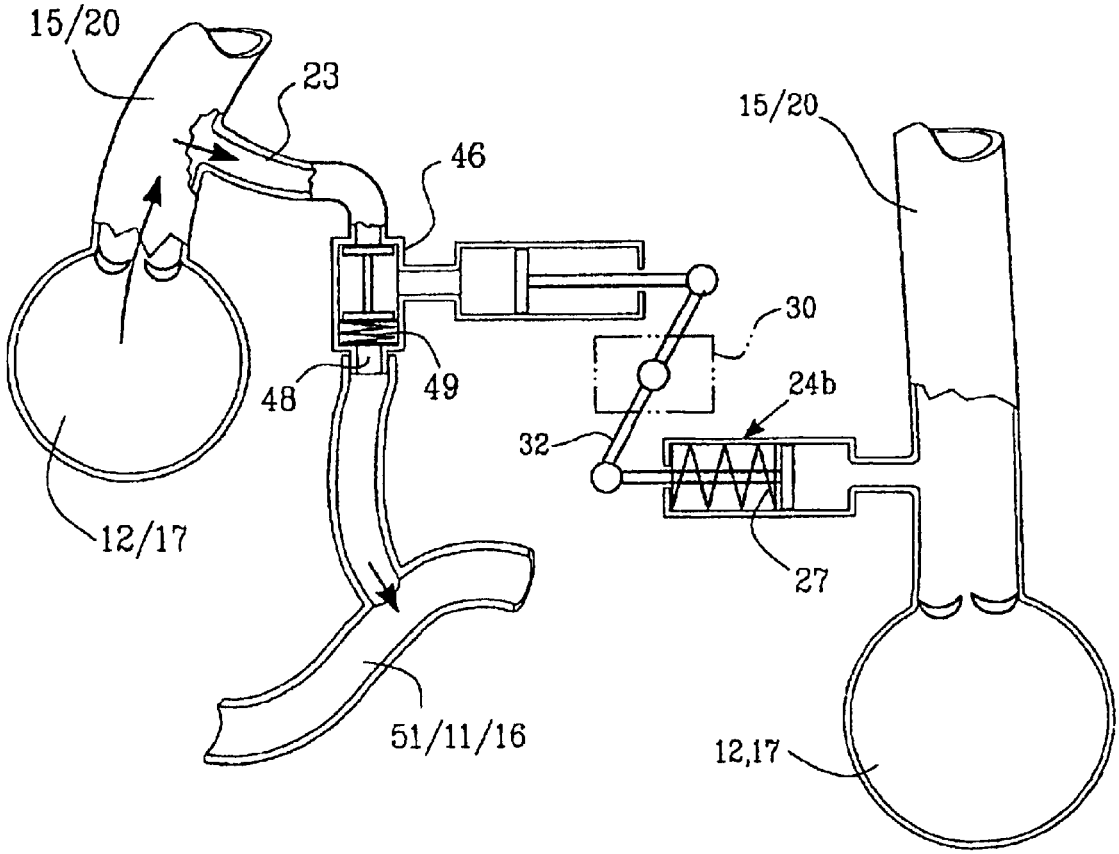
FIG. 11 demonstrates a variant of the counterpulsator demonstrated in FIG. 8.

FIG. 11 demonstrates a variant of the counterpulsator described in FIG. 8. This counterpulsator may according to FIG. 11 be connected at any location of the cardiovascular system in contrast to the one described in FIG. 8, which presumes an operation on the heart itself. A shuttle valve 46, which is connected to an artery 15 or 20, will close one port 48 of the valve at each pressure rise (systole) in the way that the hydraulic pressure can act on the hydraulic motor 24a. This motor will transmit the movement, via the gear 30, to the hydraulic pump 24b and the spring 27 will be compressed. In diastolic phase, the shuttle valve 46 opens and the blood from the hydraulic motor can return to the system at the same time as the spring 27 can expand. The hydraulic pump 24b releases the blood to the actual artery 15 or 20.

Figure 12:
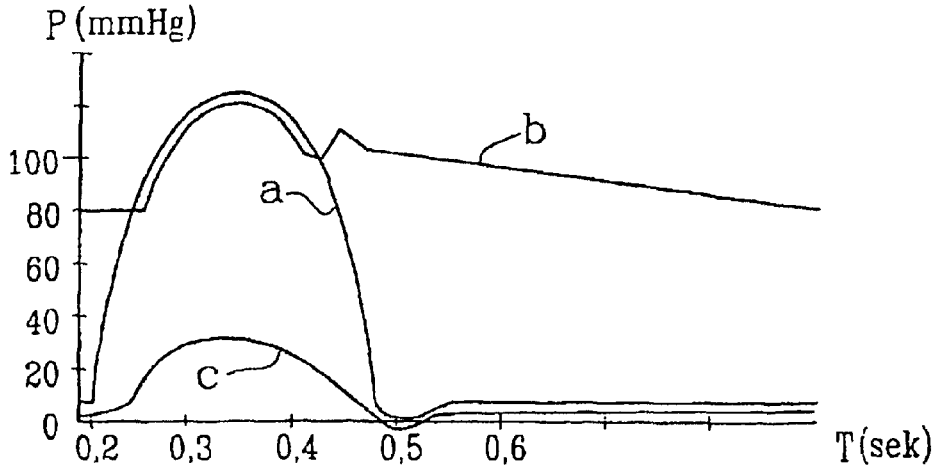
FIG. 12 demonstrates a pressure—time—diagram for a normal heart without any assist device.
Figure 13:
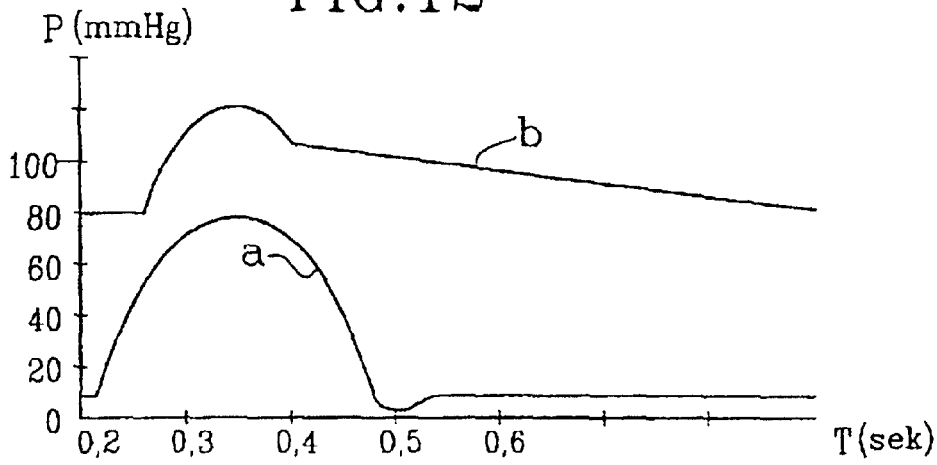
FIG. 13 demonstrates a similar pressure—time—diagram for a heart connected to a pressure amplifier according to the present invention.
Figure 14:
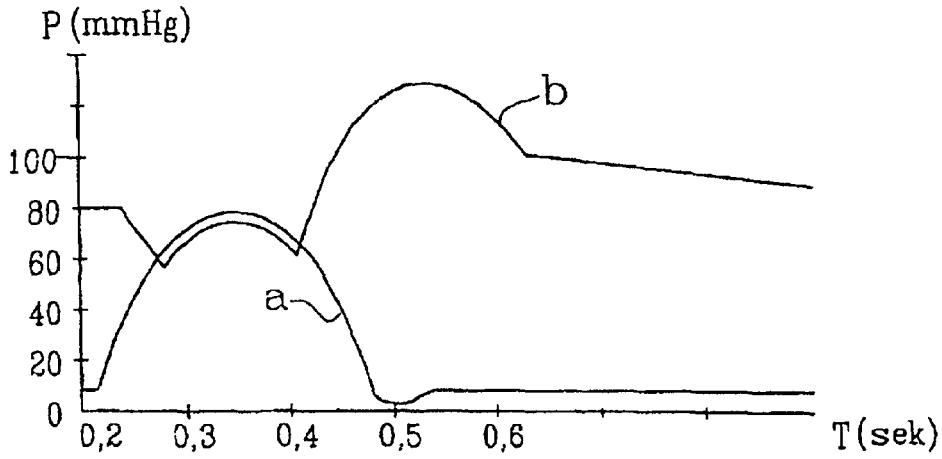
FIG. 14 demonstrates a similar pressure—time—diagram for a heart connected to a counterpulsator according to the present invention.

FIGS. 12 to 14 demonstrates the pressure curves for the ventricles in different situations. FIG. 12 illustrates the pressure in a normal heart without assist. The curve a shows the pressure in the left ventricle 12, the curve b the pressure in the aorta 15, and the curve c in the right ventricle. FIG. 13 demonstrates how a pressure amplifier according to the present invention may change—increase—the pressure in the aorta 15, while in FIG. 14 it is demonstrated how a counterpulsator, according to the present invention, may delay and increase the pressure of the artery. In both examples given—FIG. 13 and FIG. 14—the size and the profile of the curve b may be influenced by the regulating mechanism 30.

It is noted that the curve b of FIG. 13 during the complete cardiac cycle is located at a higher level than the curve a. This illustrates the unique by this invention and has not been possible previously without adding energy from outside.

Figure 15:
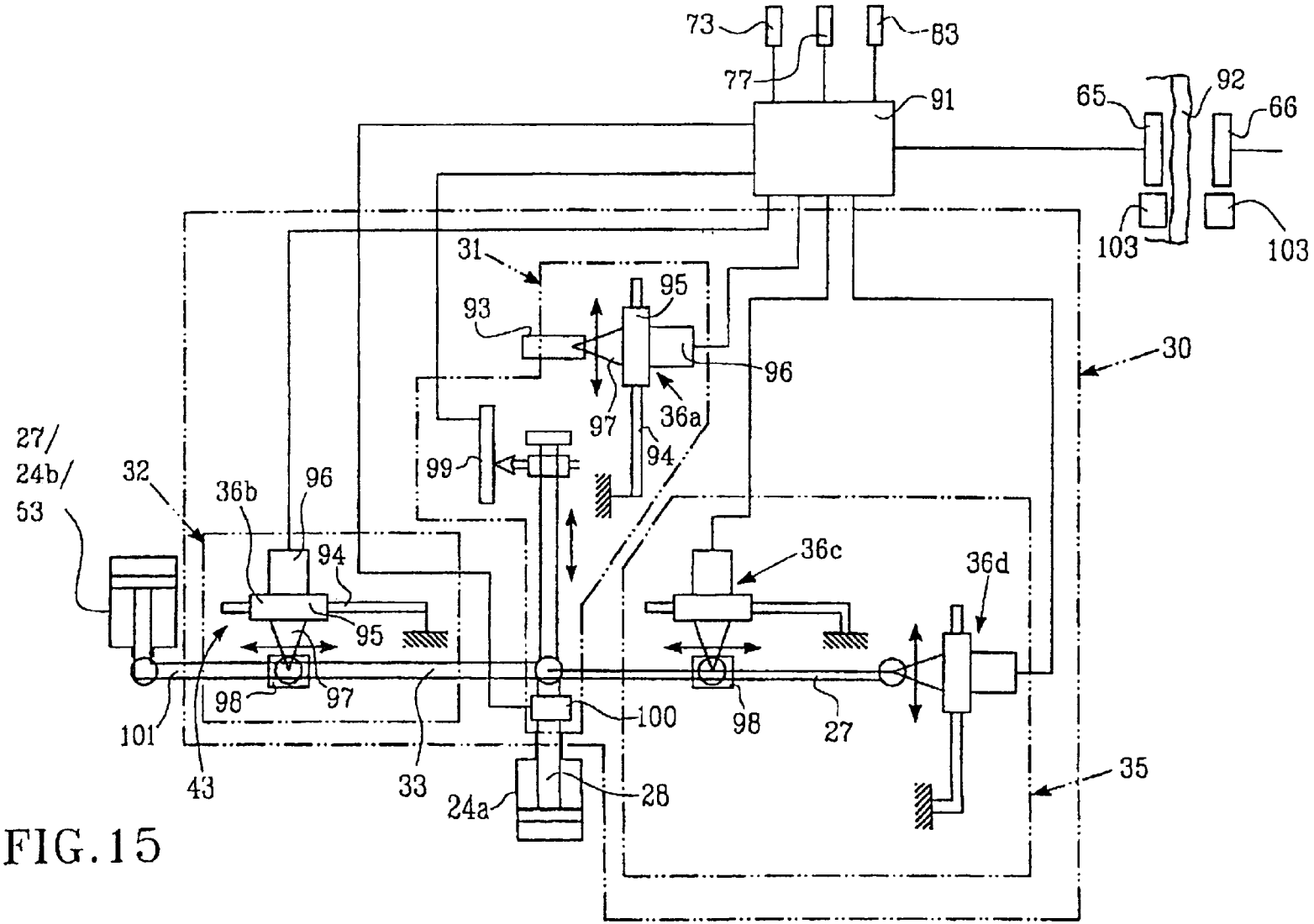
FIG. 15 demonstrates very schematically a regulating mechanism for devices according to the present invention.

FIG. 15 demonstrates above mentioned complete regulating mechanism 30, which includes a first control unit 31 for limitation of stroke of for example the piston rod 28 of the hydraulic motor 24a. A second control unit 32 exists for regulation of the gear between for example the hydraulic motor 24a and the hydraulic pump 24b, and a third control unit 35 exists for regulation of settings of the spring. Depending on the disease and the actual conditions the regulator 30 may comprise all or only some of the regulators/sensors.

The individual control units 31, 32 and 35, which are included in the regulating mechanism 30 according to FIG. 15 are all supplied with at least one regulator 36a–d. This consists of a fix rail 94 along which a trolley 95 or a slide is displaceable along the rail 94 by help of a motor 96. The trolley 95 has an arm 97 and a connector 98, which may be varied depending on what the regulator 36 is to be used for.

In the first control unit 31, the connector 98 of the regulator 36a is performed as a displaceable stop 93, limiting the stroke of the transferal organ 28 belonging to the hydraulic motor, which may be a piston rod. In this control unit 31 is included even a sensor of position 99 and a strain gauge 100.

The purpose of the second control unit 32 is to regulate the gear between the hydraulic motor 24a of the secondary unit and the piston pump 24b of the tertiary unit 29 or to regulate the gear between two secondary units. To do this, a lever 101 is arranged between the piston rods of the hydraulic motor and the pump. The pivot point is the connector 98, which is displaceable along the rail 94 in the way that a variable gear of the force from the hydraulic motor 24a to the pump 24b can be achieved. The regulation of the pivot point is performed with the adjusting means 26b. Depending on the preset parameters of the gear i.e. the pivot point of the lever 101, the quote of the energy extracted from the two ventricles may be varied, alternatively, the gear between the secondary and tertiary unit may be varied.

The third control unit 35, which controls the settings of the spring, has two adjusting devices 36c and 36d, of which the connector 98 of the first mentioned device 36c is displaceable along a spring 27 in order to adjust the tension of the spring. Using the second adjusting device 36d it is possible to adjust the zero point of the spring.

The components like the adjusting devices 36 and the sensors 99,100 in the different units 31, 32, 35 are all connected to a computer.

Figure 16:
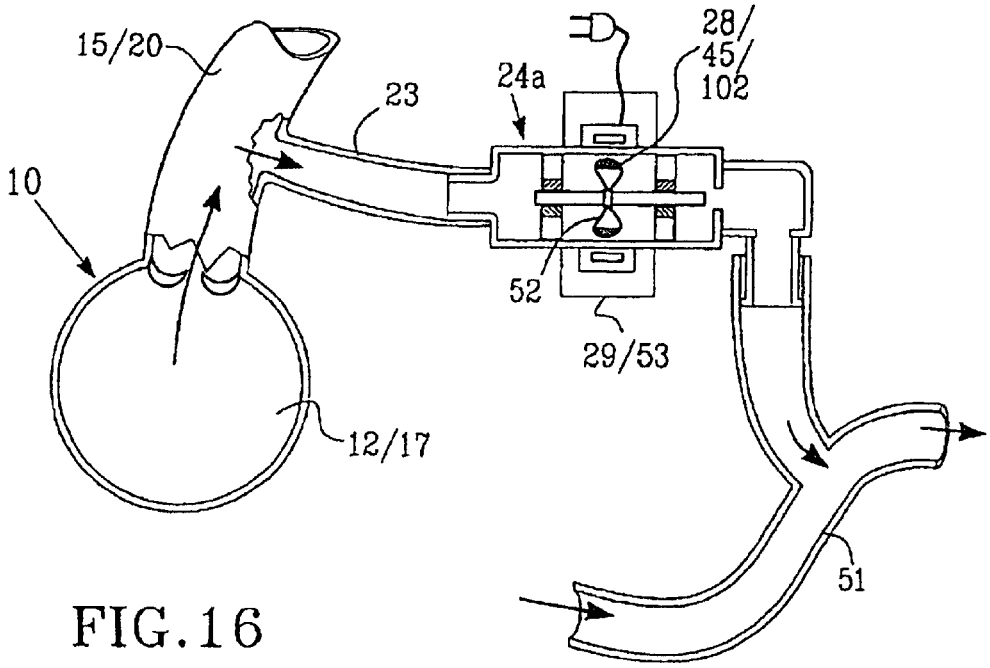
FIG. 16 demonstrates schematically a device for generation of electricity by using a hydraulic motor.

FIG. 16 gives an example of how the energy extracted from the heart can be utilized—transformed—for generation of electricity. For this purpose, the hydraulic motor 24a is connected to an artery 15/20/50 and arranged as a turbine with a magnetic propeller 52 where the majority of the energy of the blood pressing the propeller is converted to kinetic energy.

The transferal organ 28 consists in this example of a magnet connector 102, which runs a generator 53. The blood passing the turbine is returned to a vein 51.

The speed of the turbine can be regulated by means of for example adjustable flow devices (not given in the figure) and/or by rotating the wings of the propeller. The rotation energy can if necessary be stored temporarily by connecting a flywheel to the turbine shaft.

Figure 17:
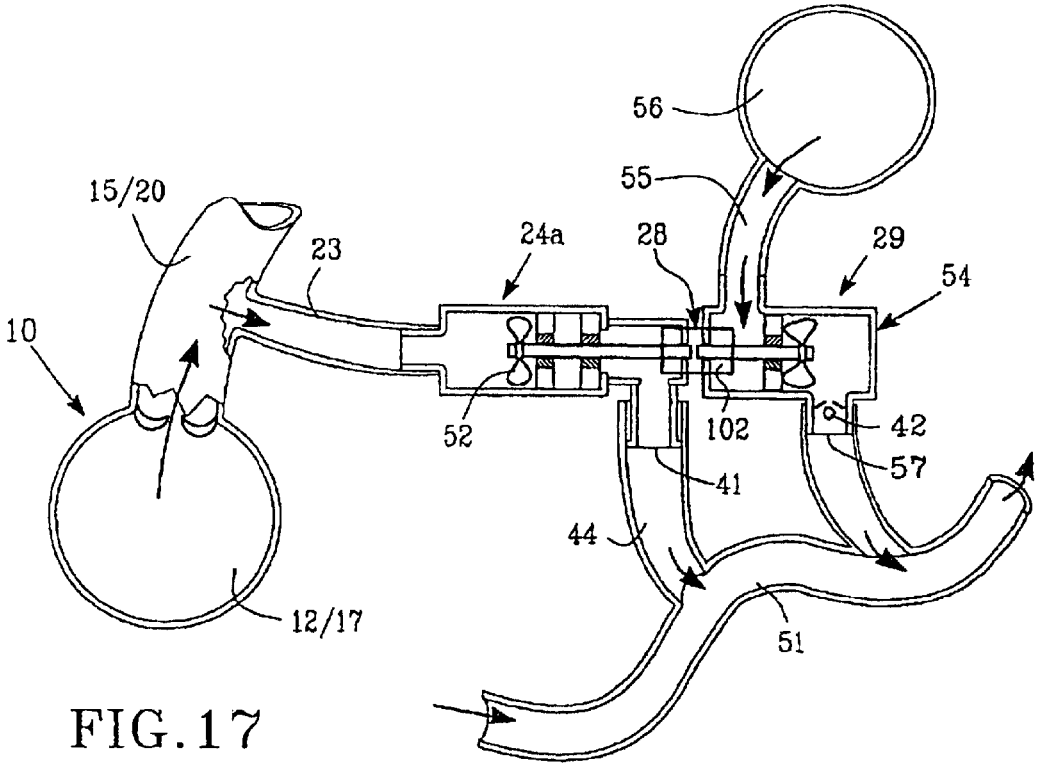
FIG. 17 demonstrates schematically a device consisting of a hydraulic motor and a hydraulic pump in a composite unit, constructed for drainage purpose of compartments of the body.

In some diseases it is necessary to drain compartments of the body for example the abdomen. This drainage is to day arranged by a tube passing out of the body through the skin. In FIG. 17 is given a system where the hydraulic energy of the blood is used to run an implantable pump 54 connected to a hydraulic rotation motor 24a. The pump 54 is connected to the actual compartment of the body 56 with a tube 55. The outlet 57 of the pump 54 and the outlet 41 of the hydraulic motor 24 are both drained to a vein 51. This means that the drained liquid is returned to the circulation of the body and a thus a continuous change is established. A valve 42 is located in the outlet of the pump 54 to inhibit retrograde inflow of blood to the hydraulic motor, pump and/or abdomen. Even in this example, the transferal organ 28 is a magnet connector 102 between the shafts of the turbine and the pump.

Figure 18:
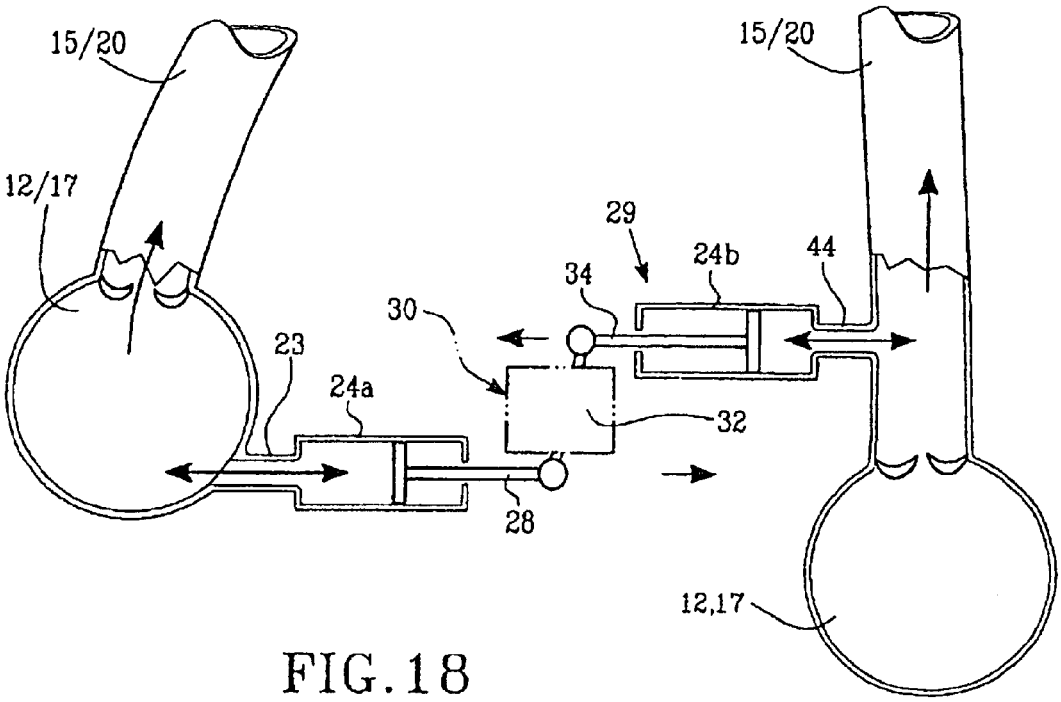
FIG. 18 demonstrates a device arranged to transfer energy from one ventricle to the contralateral circulation.

The device according to FIG. 18 is to its construction similar to the example demonstrated in FIG. 8. In this example the device is used in diseases where the efficiency of the right—or left ventricle 17, 12 is decreased, by for example an infarction, after a heart transplantation, a defect in some of the valves or the like. The hydraulic motor 24a and the piston pump 24b aims to enhance the emptying of for example the right ventricle in systolic phase, and to build up a pressure in the pulmonary artery in diastole.

Figure 19:
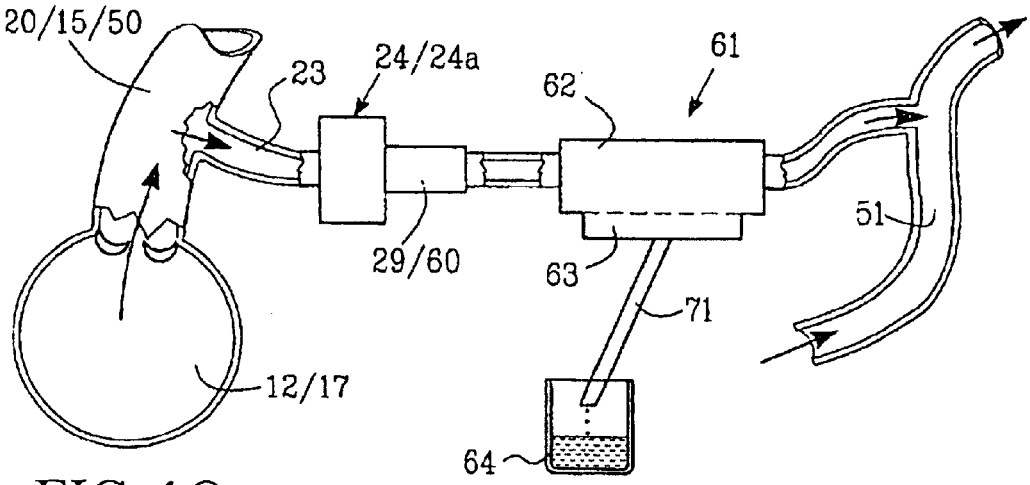
FIG. 19 demonstrates schematically an implantable device for dialysis according to the present invention.

A device according to the invention can also be used to power an implantable, or external apparatus for dialysis 61, as demonstrated in FIG. 19. Since a pressure approximately four times the mean pressure of the aorta is needed in a dialysis chamber, a pressure amplification unit 60 is needed, which is connected to the hydraulic motor 24a, thereby increasing the pressure to dialysis pressure level. The pressurized blood is transferred from the pressure amplifier to the blood side 62 of the dialysis device and thereafter to a suitable vein 51. The water side 63 of the dialysis device is via a drainage tube 71 connected with an external collector 64. Alternatively, the drainage tube is connected to the urinary bladder or to a urostomy (artificial urinary bladder/opening).

The dialysis apparatus according to the present invention results in water being lost from the body and this fluid must be replaced. Normally dialysis fluid of specific composition is added to the organism through a vein and/or by drinking. Since filtration in a dialysis filter results in the blood becoming more viscous on its way through the filter (since dialysed water is eliminated) in some dialysis apparatus extra dialysis liquid is added before the filter unit (i.e. predilution), Such predilution will enhance the flow through the filter.

Figure 20:
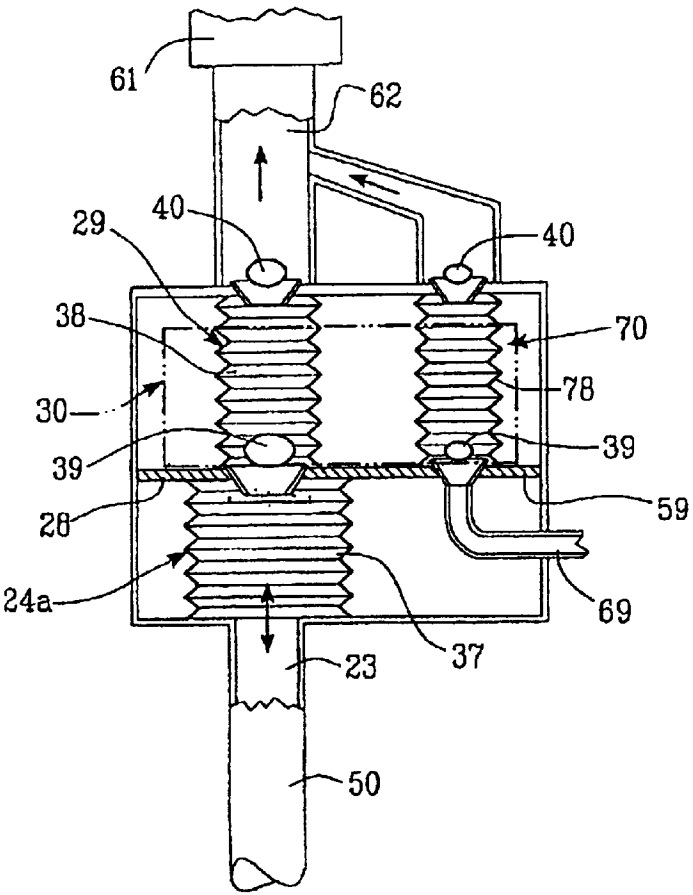
FIG. 20 demonstrates schematically an implantable device for dialysis supplied with pressure amplifier and predilution mechanism. Water for dialysis is automatically added before the filter unit.

The device according to FIG. 20 demonstrates a principle illustration of an automatic pressure amplifier with build in predilution pump 70. Parallel with the movements of the pressure amplifier 29, moves a secondary bellows 78, which delivers specific dialysis liquid through a tube 69, bypassing the valves 39 and 40, to the high pressure side 62 of the filter unit of the dialysis device 61. By arranging correct dimensions of the two bellows 38 and 78, a specific predilution of the blood is achieved.

Figure 21:
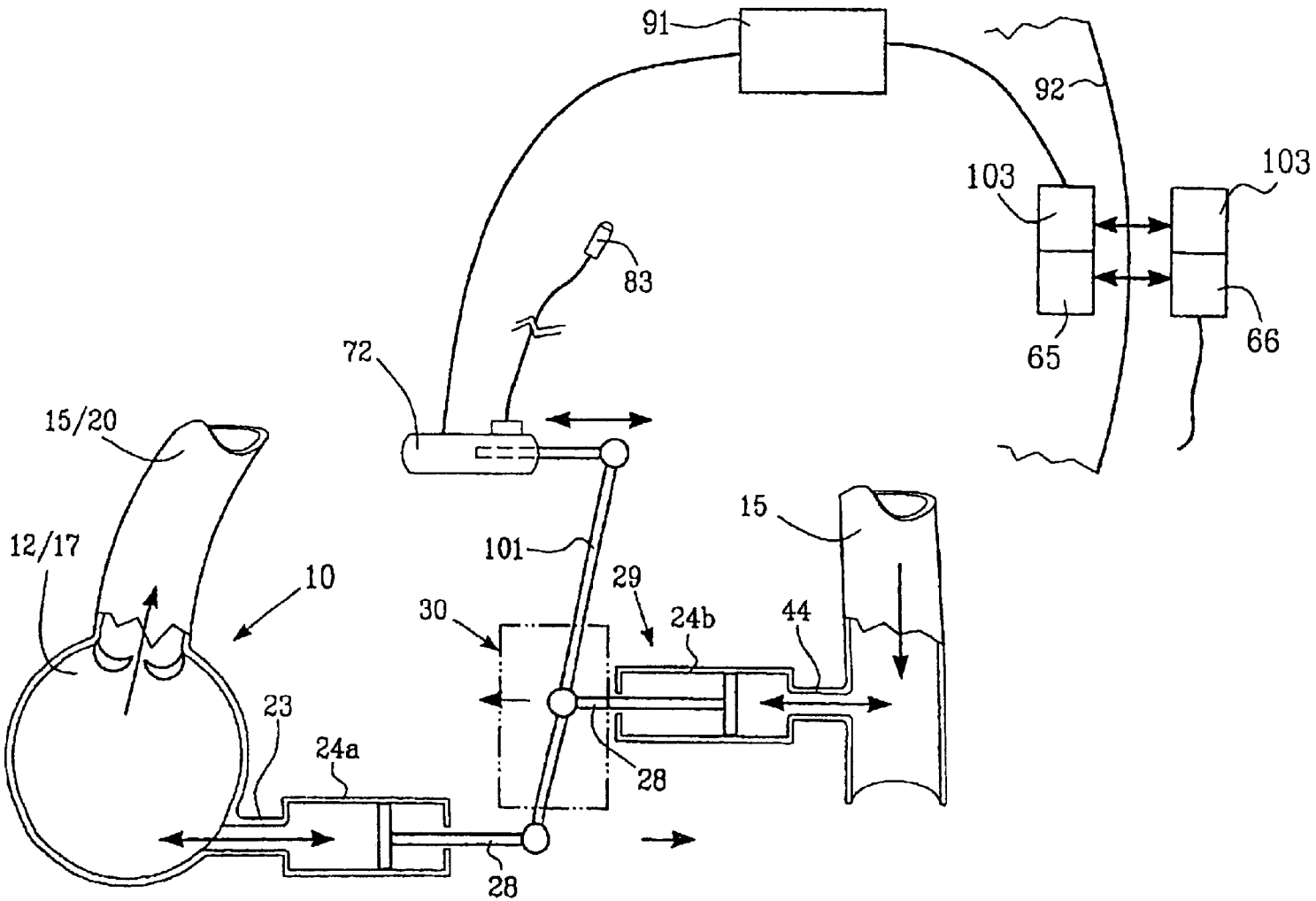
FIG. 21 demonstrates schematically a device according to FIG. 8, which in addition is connected to a combined motor and generator.

FIG. 21 demonstrates an example where the device of FIG. 8 can be used as a continuously working counterpulsator but also, preferably when the patient is at rest, as a generator of electricity 72. This generator can charge a battery 65 (an electric accumulator), permitting high energy output when needed. The battery is preferably located in the way that it may be charged by a charger 66 outside the body near the skin 92. The electrogenerator 72 can even be run as an electromotor with power from the battery 65 to assist the heart temporarily when needed. The switch (from generator to motor) can be facilitated by a detector, for example a piezeo-electric sensor 83, detecting a certain condition of the body. At specific changes of such condition, the generator function is charged to motor function or the opposite. Even an external signal may be responsible for this change in function mode.

Figure 22:
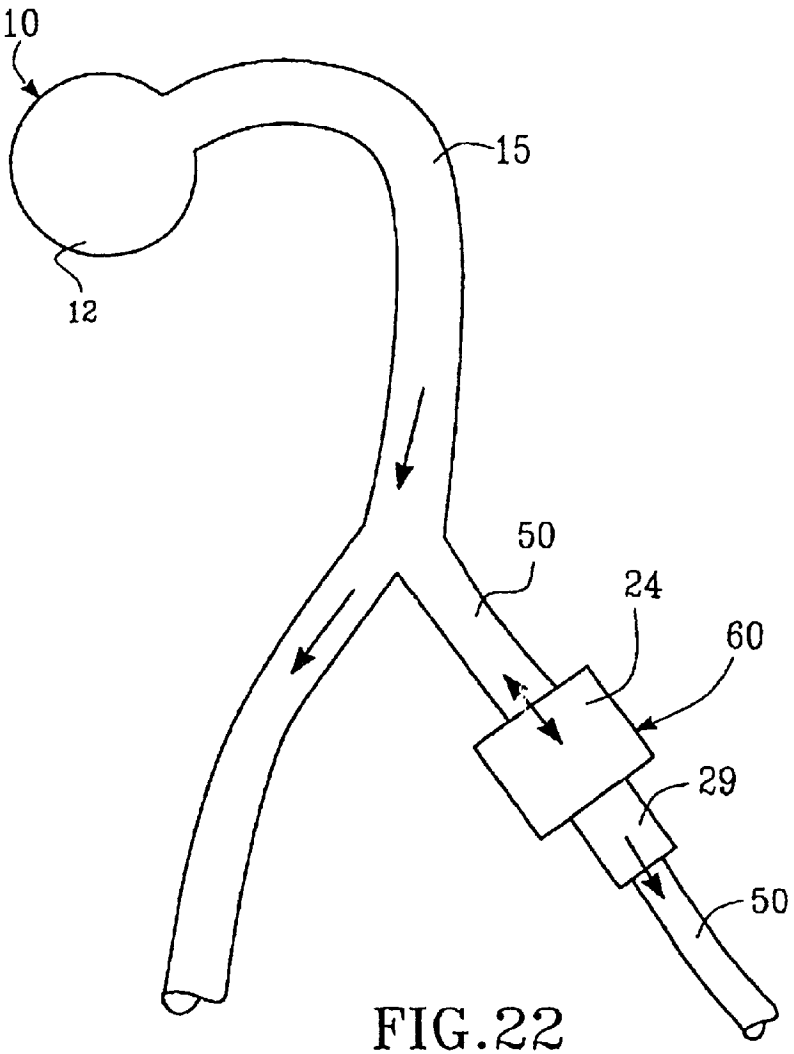
FIG. 22 demonstrates a device according to the present invention arranged as a pressure amplifier placed in a specific organ like for example a leg.

FIG. 22 demonstrates a device according to the invention arranged as a pressure amplifier 60, in this example implanted in a leg, connected to an artery 50 to accomplish an enhanced circulation of a foot.

Figure 23:
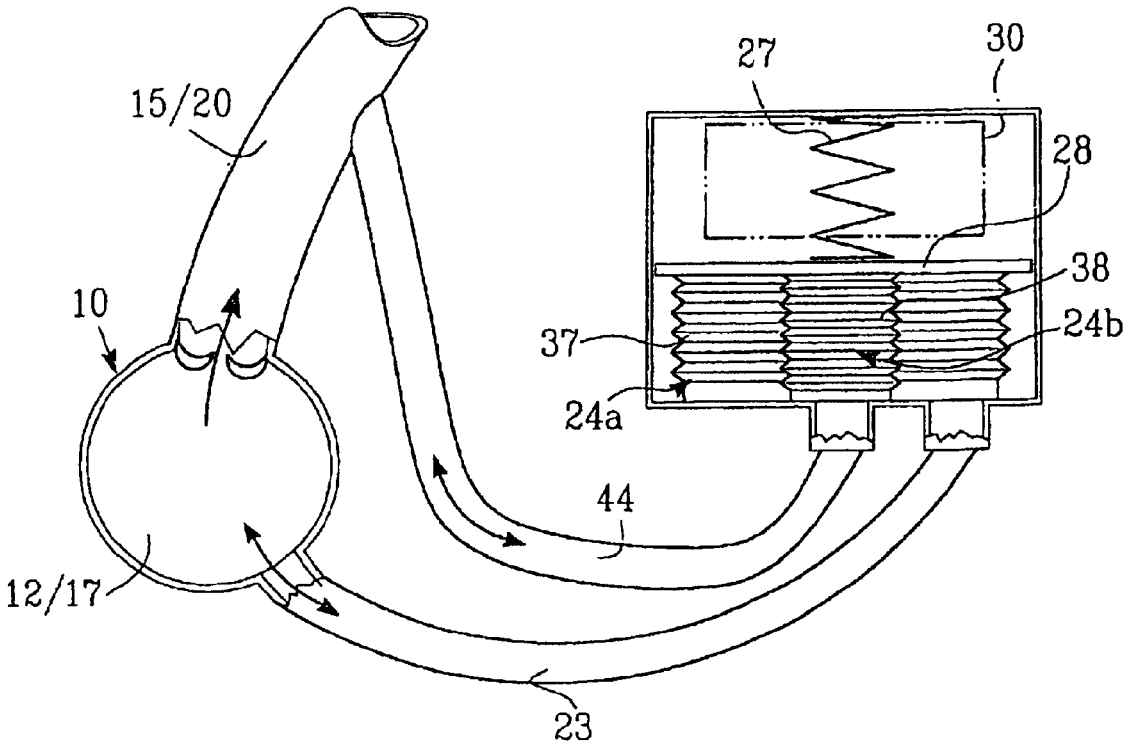
FIG. 23 demonstrates a variant of the device according to FIG. 8 arranged as a counterpulsator.

FIG. 23 demonstrates an additional variant of a counterpulsator where the hydraulic motor and the executing device 29, i.e. the pump 24b, consist of concentric bellows 37 and 38 which are interconnected by a common transferal organ 28—a pusher plate—located within each other to accomplish a flat construction.

Figure 24:
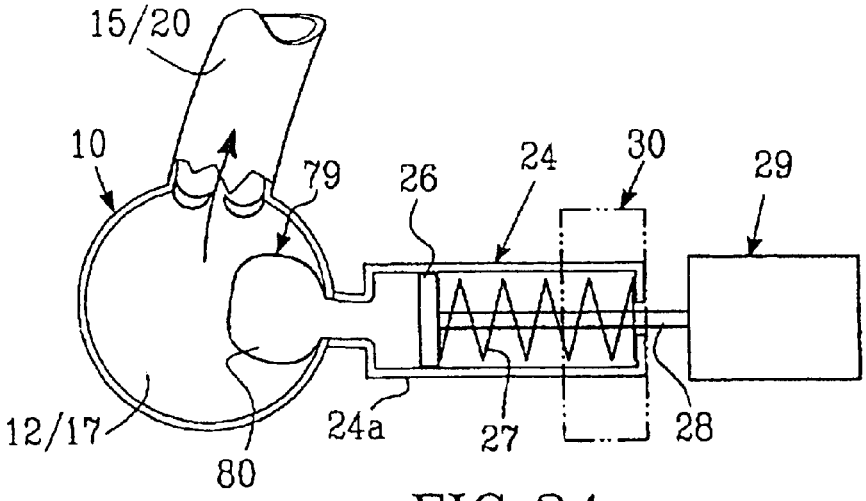
FIG. 24 demonstrates a variant of the device according to FIG. 4 arranged with a closed circuit pressure medium system.

FIG. 24 demonstrates a variant of the invention where the heart 10 and the secondary unit 24 are connected indirectly. In stead of having the blood acting on the piston 26 of the hydraulic mtor 24a, a membrane 79 is arranged as an elastic sack 80, connected to the heart, and connected to the hydraulic motor. The sack is filled with an alternative fluid without direct contact to the blood. This variant can principally be used in all examples, when an indirect connection is wanted. The membrane in this example located as a sack in the ventricle, but the membrane can principally be located in any part of the body where the pump activity of the heart is to be utilized. Two such examples are given in FIG. 25 and 26. According to FIG. 25, a second sack 81 has been connected to the second bellows 38 of the hydraulic motor 24a. This sack 81 is located within an artery 50 and can there make contraction—expansion movements.

Figure 26:
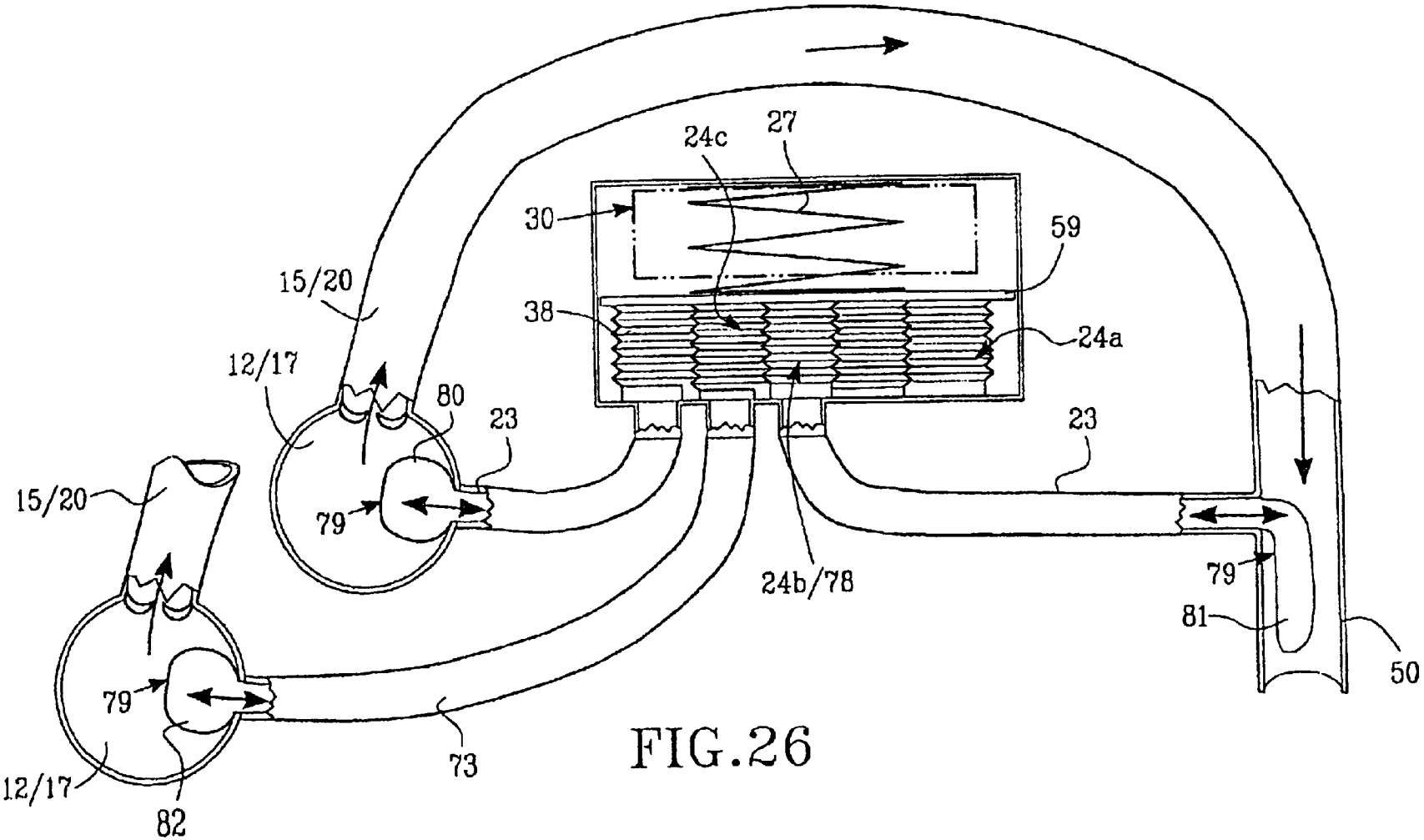

In the example according to FIG. 26, the secondary unit 24 has been given a triple function by arranging the hydraulic motor 24a with a third bellows 78 and a third sack 82. The three systems cooperate as a counterpulsator taking out energy from both ventricles and delivering to an artery.

Figure 27:
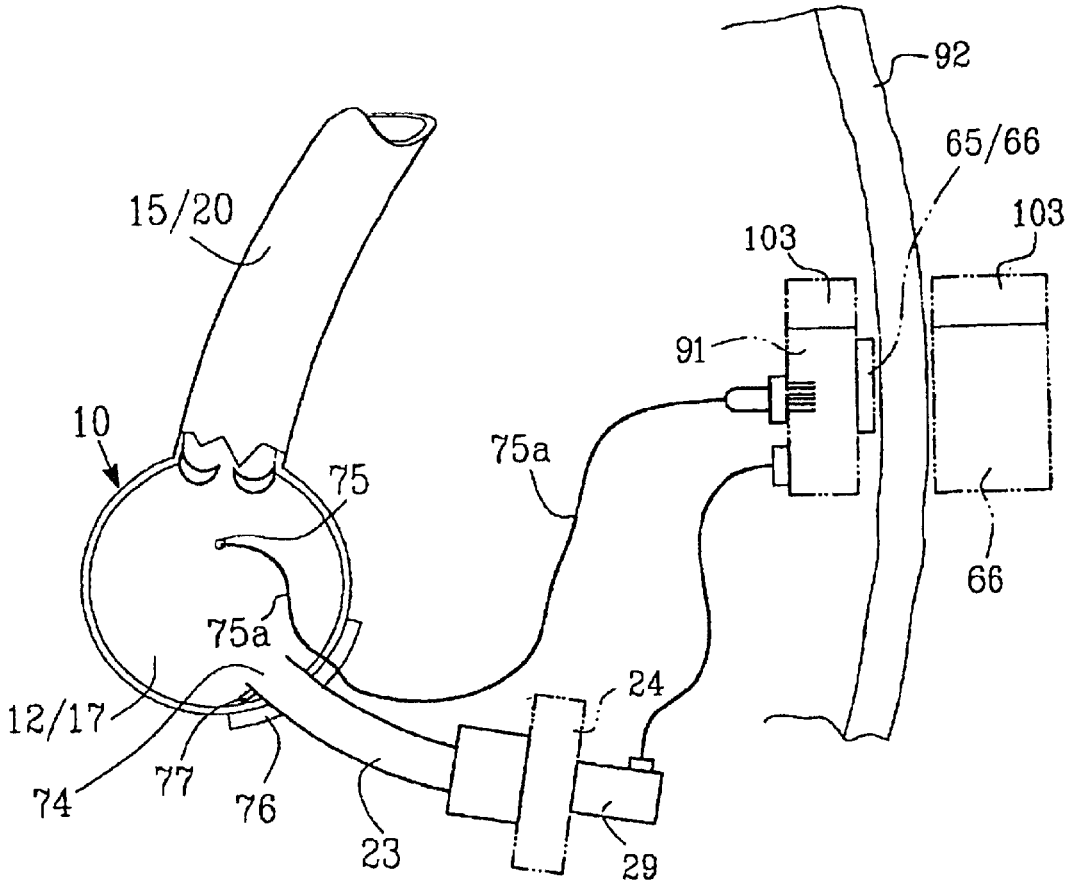
FIG. 27 demonstrates a ventricle containing a gauging device.

FIG. 27 demonstrates schematically a ventricle 12 or 17 to which is connected a tube 23. This tube is connected to a secondary unit 24 not to be further specified since its characteristics are unimportant for the description of this example. The tube 23 includes a fixation device 76, having the form of a cuff preferably produced by some soft material like for example Teflon. The purpose of the cuff is fixation of the tube 23 to the heart 10. This construction is well known within heart surgery. Through the opening 74 into the heart, where the tube 23 passes, or through the tube 23 itself, is arranged a catheter 75a, a cable or similar, to a sensor 75 at the inside of the ventricle 12 or 17 for continuously monitoring of the volume and pressure conditions of the ventricle. Such catheters do exist commercially on the marker like for example catheters of impedance type. It is also possible to arrange fix sensors 77 at the fixation device itself. Signals from such sensors are used for regulation of the secondary—and/or tertiary units 24, 29, sometimes via a processor (a computer) 91, which may be powered with electricity from a tertiary unit. The processor 91 is preferably inoperated under the skin 92 in the way that the accumulator 65 can be charged from a battery charger located outside the body.

The invention is not limited to above described examples but several other variants and combinations are possible within the limits of the patent claims.

The device is not useful in all situations of heart failure. If a ventricle is little and stiff with a low compliance, the device for natural reasons cannot extract big volumes from the ventricle and therefore the absorbed energy is limited. In contrast, the device can absorb energy from one side of the circulation (left or right) and give back the energy to the opposite side without blood flow from one side to the other. This has so far been impossible with any known pump. The present pump thus can be connected to the contralaterat side of the heart as well as to the homolateral side. For natural reasons the extraction of energy from the left side of the circulation delivered to the right side can be higher and more powerful since the left side of the heart normally is 5 times as strong as the right side. But the opposite way around can also be of significant importance in critically ill patients.

Thus, the energy potentially delivered by the heart may therefore be:

A Be given back to the circulation at the same cycle;

B Be stored and given in return later;

C Be converted to electricity and used within or outside the body;

D Be used for the control of mechanisms of the body itself;

E Generate pressure to be used for running an artificial kidney outside or within the body;

F Pump liquid from one compartment of the body to another;

G Pump liquid from inside the body to the outside—or the opposite;

H Operate valves within or outside the body, to control natural or artificial openings of the body;

I Supply pacemakers or other electric pulsgenerators like ICD apparatus with power;

J Stimulate peripheral nerves (like for example the rhythm of ventilation);

K Supply implantable computers or similar equipment with energy;

L Supply implantable electric devices with energy, such devices being in contact with the central nervous system to detect nerve potentials and computerize these and give signals in return to the nervous system, other organs or artificial apparatus in the same area or at a distance in order to facilitate operational functions. One example may be computers being able to bridge a defect of the spinal cord or bridge nerves with an interrupted continuity.

10 The heart
11 Left atrium
12 Left ventricle
13 The mitral valve
14 The aortic valve
15 The aorta
16 Right atrium
17 Right ventricle
18 The tricuspid valve
19 The pulmonary valve
20 The pulmonary artery
21 Caval veins
22 Pulmonary veins
23 Connecting tube
24a Secondary unit
24b Hydraulic motor
25 Volume chamber/cylinder/bellows
26 Piston
27 Spring
28 Transferal organ
29 Tertiary unit/effector organ
30 Regulator
31 First regulator for stroke
32 Second regulator of gear
33 Lever
34 Piston rod
35 Third regulator for preset of spring parameters
36a,b,c,d Regulators
37 First bellows
38 Second bellows
39,40 Unidirectionally functioning valves
41 Connection tube
42 Stop valve
43 Regulator
44 Tube
45 Generator
46 Shuttle valve
47 First opening
48 Second opening
49 Spring
50 Artery
51 Vein
52 Turbine propeller
53 Electric generator
54 Pump
55 Drain tube
56 Compartment of body
57 Outlet from pump
58 Outlet from hydraulic motor
59 Pusher plate
60 Pressure amplifier
61 Apparatus for dialysis
62 Blood side
63 Water side
64 Container
65 Electric accumulator
66 Charging device
67 First opening
68 Second opening
69 Tube for predilution water
70 Predilution pump
71 Drain tube
72 Combined electric-generator/electric-motor
73 Hydraulic fluid
74 Opening of the heart
75 Device for registration
76 Device for fixation
77 Sensor
78 Third bellows
79 Membrane
80 First balloon
81 Second balloon
82 Third balloon
83 Gauge device
90 Electric connector
91 Computer
92 Skin
93 Stop for limitation of stroke
94 Rail
95 Car
96 Motor
97 Attachment arm
98 Connector
99 Potentiometer
100 Strain gauge
101 Lever
102 Magnetic connector
103 Data communication port
104 Valve
110 Conus

What is claimed is:

1. A device for implantation, able to make use of at least part of the hydraulic energy generated by a heart at its natural phases of work, said device including at least one actuator connected to the cardiovascular system of an organism, said actuator arranged in order to transfer the hydraulic energy to an executive organs, said executive organ arranged to influence certain defined functions within or outside the organisms, characterised by the actuator consisting of a hydraulic motor located outside the cardiovascular system of the organism, said hydraulic motor arranged to conduct at least part of the hydraulic fluid to and fro between the hydraulic motor and its connecting site to the organism, and/or between arteries and/or veins and that the executive organ consists of at least one pump powered by the hydraulic motor, said pump delivering hydraulic fluid to and fro vessels synchronously or asynchronously in relation to the rhythm of the heart with or without pressure amplification.

2. A device according to claim 1, wherein a regulating mechanism is arranged between the hydraulic motor and the pump for adjusting running parameters of the device.

3. A device according to claim 1, wherein the hydraulic motor is connected to more than one pulsating pressure source.

4. A device according to claim 1, wherein the hydraulic motor is a deplacement motor, and that one of a piston rod and a pusher plate is connected to one of a piston and a membrane of the deplacement motor and that the executive organ is one of a piston pump, and a pressure amplifier.

5. A device according to claim 1, wherein the hydraulic motor (24) is a rotation motor for example a turbine and that the executive organ (29) is a rotation pump (54) or a similar device, and that a magnetic connection (102) or a similar device is arranged between the hydraulic motor (24) and the executive organ (29). (FIGS. 16, 17).

6. A device according to claim 1, wherein the hydraulic motor, the executive organic and a transferal organ arranged in between the hydraulic motor and the executive organ are integrated in one unit.

7. A device according to claim 6, wherein the hydraulic motor (24a) is a first bellows (37) influenced by a spring and the transferal organ (28) is a pusher plate (59) connected to said first bellows, said pusher plate includes an opening (67) supplied with a stop valve (39) and that the executive organ (29) is a second bellows (38) connected to said pusher plate (59) of said first bellows (37) and that said second bellows is configured with a cross sectional area being different to the cross sectional area of said first bellows (FIGS. 6, 20).

8. A device according to claim 1, wherein the hydraulic motor (24a) consists of two piston— or bellows motors (24a), working in parallel, each motor connectable to a ventricle of the heart (12, 17) and where said motors are interconnected by a regulating mechanism (30), (FIG. 5).

9. A device according to claim 4, wherein the pressure side of said hydraulic motor (24a) and the piston pump (24b) are arranged to communicate with each other through a connection tube (41) containing a stop valve (3) and that the piston—and pump rods (28, 34) are interconnected via a regulating mechanism (30), (FIG. 7).

10. A device according to claim 4, wherein the piston pump has a piston rod, the piston rods of the hydraulic motor and of the piston pump being interconnected via a regulating mechanism as a counterpulsator.

11. A device according to claim 1, wherein a shuttle valve (46) is included at the anterior aspect of the hydraulic motor (24a) and that said shuttle valve is arranged to be able to establish connection between the heart and the hydraulic motor in the contraction phase of the heart while being able to establish connection between the hydraulic motor and a vein (51) in the relaxation phase of the heart (FIG. 10).

12. A device according to claim 1, wherein the hydraulic motor (24a) is arranged to power a pump (54), said pump having a n inflow opening which is connected to a compartment of the body (56) and having an outflow opening (57) being connectable to the circulatory system of the body (FIG. 17).

13. A device according to claim 1, wherein the hydraulic motor (24) is connected to a pump working as a pressure amplifier (60), said pump arranged to raise the blood pressure to dialysis pressure, and that said amplifier is connected to the blood side (62) of an implanted apparatus for dialysis (61) while the water side (63) of the dialysis apparatus is connected with a tube (71) for transport of liquid of the body (FIG. 19).

14. A device according to claim 1, wherein the hydraulic motor (24) is arranged to power a predilution pump (70) parallel with the executive organ (29), (FIG. 20).

Figure 25:
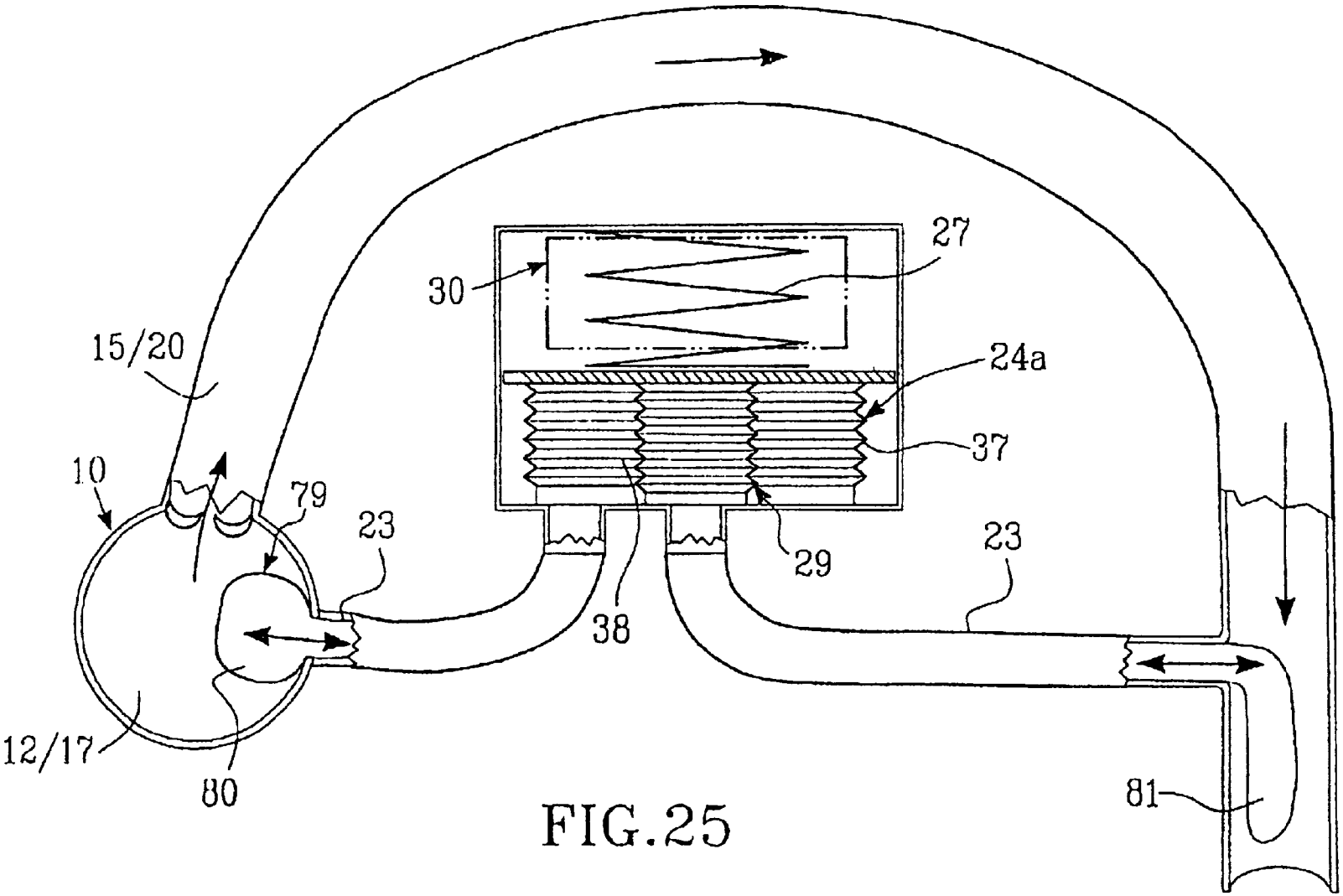
FIG. 25 demonstrates a variant of the device according to FIG. 8 arranged with a double closed circuit medium system FIG. 26 demonstrates a modification of the device according to FIG. 25 arranged with a triple closed circuit medium system.

15. A device according to claim 7, wherein the bellows (37) active as hydraulic motor (24a) contains at least one other bellows (38) and the said bellows is arranged as a pump (38), and that the first and second bellows share a common pusher plate (59) adjusted by a regulating mechanism (30) in one end and that each bellows has its fluid connection at the other end (FIGS. 23,25).

16. A device according to claim 15, wherein a third bellows (78) is arranged concentrically within existing first and second bellows (37,38) and that two of the bellows are connected to each a ventricle of the heart while the third bellows is connected to an artery (50), (FIG. 26).

17. A device according to claim 1, wherein at least one membrane (79) is arranged between the heart (10) and the hydraulic pump (24) and/or between the hydraulic pump and the executive organ (29), said membrane being for example a bladder (80, 81, 82) or a similar device, said membrane arranged to separate the blood side form the hydraulic fluid of the corresponding unit (FIG. 25,§).

18. A device according to claim 10, wherein the hydraulic motor (24a) is connected to one ventricle (17/12) of the heart (10) and that the pump (24b) acting as counterpulsator is connected to an artery deriving from the other ventricle (17/12) resulting in an action where one ventricle powers the hydraulic motor (24a) in systolic phase, while in diastolic phase a pressure is generated in the artery (15/20) of the opposite side. (FIG. 18).

19. A device according to claim 1, wherein sensors (77), gauges (83) and/or registering devices (75) are located within the organism in order to detect or quantify specific functions of the body, with the purpose to influence the regulation of the hydraulic motor (24) and/or the executive organ (29). (FIGS. 15,21,27).

20. A device according to claim 19, wherein signals from said sensors, gauges or registering devices are arranged to be processed by a preferably implanted computer (91). (FIG. 27).

21. A device according to claim 1, wherein a regulating mechanism (30) is arranged and includes different control units (31,32,33), said control units being arranged to be adjusted or regulated by a preferably implanted computer (91) and that said computer is arranged to communicate with the surrounding via a data port located under the skin.

22. A device according to claim 21, wherein the regulating mechanism (30) includes a first control unit (31) for limitation of stroke of for example the piston rod (28) of the hydraulic motor (24a), and/or includes a second control unit (32) for regulation of the gear between the hydraulic motor (24a) and the hydraulic pump (24b) and/or includes a third control unit (35) for regulation of the settings of the spring.

23. A device according to claim 1, wherein the device includes a shuttle valve (46) in the system after the hydraulic motor (24a) in the direction of the flow, said shuttle valve arranged to close one first opening of the valve (48) against a vein each time pressure is raised, while at the same time open the port connected to the hydraulic motor or a similar device. (FIG. 11).

24. A device according to claim 4, wherein the displacement motor is one of a piston motor, a compression chamber and a bellows.

* * * * *